(12) United States Patent
Chiu et al.

(10) Patent No.: US 11,529,127 B2
(45) Date of Patent: Dec. 20, 2022

(54) METHODS AND APPARATUSES FOR PROCESSING ULTRASOUND SIGNALS

(71) Applicant: BFLY Operations, Inc., Guilford, CT (US)

(72) Inventors: Leung Kin Chiu, Branford, CT (US); Karl Thiele, St. Petersburg, FL (US); Nevada J. Sanchez, Guilford, CT (US); Sheng-Wen Huang, Guilford, CT (US)

(73) Assignee: BFLY OPERATIONS, INC., Guilford, CT (US)

( * ) Notice: Subject to any disclaimer, the term of this patent is extended or adjusted under 35 U.S.C. 154(b) by 234 days.

(21) Appl. No.: 16/910,783

(22) Filed: Jun. 24, 2020

(65) Prior Publication Data

US 2020/0405271 A1    Dec. 31, 2020

Related U.S. Application Data

(60) Provisional application No. 62/866,234, filed on Jun. 25, 2019.

(51) Int. Cl.
*A61B 8/00* (2006.01)
*A61B 8/14* (2006.01)
*A61B 8/12* (2006.01)

(52) U.S. Cl.
CPC .............. *A61B 8/54* (2013.01); *A61B 8/4444* (2013.01); *A61B 8/4494* (2013.01); *A61B 8/12* (2013.01); *A61B 8/145* (2013.01); *A61B 8/4236* (2013.01)

(58) Field of Classification Search
CPC ........ A61B 8/54; A61B 8/4444; A61B 8/4494; A61B 8/12; A61B 8/145; A61B 8/4236; A61B 8/5207; G01S 15/8925; G01S 7/52034
See application file for complete search history.

(56) References Cited

U.S. PATENT DOCUMENTS

| 5,680,863 | A | 10/1997 | Hossack et al. |
| 6,441,783 | B1 * | 8/2002 | Dean .................. G01S 7/032 |
| | | | 342/372 |
| 8,792,305 | B2 | 7/2014 | Booij et al. |

(Continued)

FOREIGN PATENT DOCUMENTS

| WO | WO 2017/222964 A1 | 12/2017 |
| WO | WO 2018/052702 A1 | 3/2018 |
| WO | WO 2019/099638 A1 | 5/2019 |

OTHER PUBLICATIONS

PCT/US2020/039363, Sep. 25, 2020, International Search Report and Written Opinion.

(Continued)

*Primary Examiner* — Christopher Koharski
*Assistant Examiner* — Taylor Deutsch
(74) *Attorney, Agent, or Firm* — Osha Bergman Watanabe & Burton LLP

(57) ABSTRACT

Ultrasound apparatus and methods of processing signals are described. The ultrasound apparatus may include multiple channels. In some embodiments, signal processing techniques are described, which in some embodiments are performed on a per-channel basis. The signal processing techniques may involve using down-conversion and filtering of signals on multiple channels. The down-conversion and filtering may be done prior to beamforming.

19 Claims, 10 Drawing Sheets

(56) References Cited

U.S. PATENT DOCUMENTS

| | | | |
|---|---|---|---|
| 9,229,097 B2 | 1/2016 | Rothberg et al. | |
| 9,473,136 B1 | 10/2016 | Chen et al. | |
| 9,479,232 B1* | 10/2016 | Loui | H04B 7/0617 |
| 9,521,991 B2 | 12/2016 | Rothberg et al. | |
| 9,592,030 B2 | 3/2017 | Rothberg et al. | |
| 9,933,516 B2 | 4/2018 | Chen et al. | |
| 10,014,871 B2 | 7/2018 | Chen et al. | |
| 10,702,242 B2 | 7/2020 | de Jonge et al. | |
| 10,709,415 B2 | 7/2020 | Neben et al. | |
| 2004/0056799 A1* | 3/2004 | Sinsky | H01Q 3/267 |
| | | | 342/368 |
| 2004/0101069 A1 | 5/2004 | Raby | |
| 2007/0129632 A1* | 6/2007 | Voie | A61B 8/4483 |
| | | | 600/438 |
| 2009/0256640 A1* | 10/2009 | Reilly | G06F 1/0328 |
| | | | 331/45 |
| 2009/0326375 A1 | 12/2009 | Magee | |
| 2010/0305449 A1 | 12/2010 | Wegener et al. | |
| 2011/0012662 A1 | 1/2011 | Ma et al. | |
| 2011/0055447 A1 | 3/2011 | Costa | |
| 2015/0280841 A1* | 10/2015 | Gudovskiy | H04L 27/2271 |
| | | | 375/226 |
| 2016/0216368 A1* | 7/2016 | Phillips | G01S 7/2921 |
| 2017/0180175 A1* | 6/2017 | Kong | H04B 7/0413 |
| 2017/0202608 A1* | 7/2017 | Shelton, IV | A61B 17/320092 |
| 2017/0202609 A1* | 7/2017 | Shelton, IV | A61B 18/1445 |
| 2017/0360399 A1 | 12/2017 | Rothberg et al. | |
| 2017/0360401 A1 | 12/2017 | Rothberg et al. | |
| 2017/0360402 A1 | 12/2017 | de Jonge et al. | |
| 2017/0360403 A1 | 12/2017 | Rothberg et al. | |
| 2017/0360404 A1 | 12/2017 | Gafner et al. | |
| 2017/0360411 A1 | 12/2017 | Rothberg et al. | |
| 2017/0360412 A1 | 12/2017 | Rothberg et al. | |
| 2018/0325490 A1 | 11/2018 | Ku et al. | |
| 2018/0364200 A1 | 12/2018 | Chen et al. | |
| 2018/0366102 A1 | 12/2018 | Ralston et al. | |
| 2019/0142388 A1 | 5/2019 | Gonyeau et al. | |
| 2019/0307428 A1 | 10/2019 | Silberman et al. | |
| 2020/0046314 A1 | 2/2020 | Neben et al. | |
| 2020/0129151 A1 | 4/2020 | Neben et al. | |
| 2020/0155113 A1 | 5/2020 | Neben et al. | |

OTHER PUBLICATIONS

International Search Report and Written Opinion dated Sep. 25, 2020 in connection with International Application No. PCT/US2020/039363.

International Preliminary Report on Patentability for International Application No. PCT/US2020/039363, dated Jan. 6, 2022.

* cited by examiner

METHODS AND APPARATUSES FOR PROCESSING ULTRASOUND SIGNALS

CROSS-REFERENCE TO RELATED APPLICATIONS

The present application claims the benefit under 35 U.S.C. § 119(e) of U.S. Patent Application Ser. No. 62/866,234, filed Jun. 25, 2019 and entitled "METHODS AND APPARATUSES FOR PROCESSING ULTRASOUND SIGNALS," which is hereby incorporated by reference herein in its entirety.

FIELD

Generally, the aspects of the technology described herein relate to processing ultrasound signals. Certain aspects relate to generating waveforms with frequencies that vary in time for down-converting ultrasound signals.

BACKGROUND

Ultrasound devices may be used to perform diagnostic imaging and/or treatment, using sound waves with frequencies that are higher than those audible to humans. Ultrasound imaging may be used to see internal soft tissue body structures. When pulses of ultrasound are transmitted into tissue, sound waves of different amplitudes may be reflected back towards the probe at different tissue interfaces. These reflected sound waves may then be recorded and displayed as an image to the operator. The strength (amplitude) of the sound signal and the time it takes for the wave to travel through the body may provide information used to produce the ultrasound image. Many different types of images can be formed using ultrasound devices. For example, images can be generated that show two-dimensional cross-sections of tissue, blood flow, motion of tissue over time, the location of blood, the presence of specific molecules, the stiffness of tissue, or the anatomy of a three-dimensional region.

SUMMARY

According to an aspect of the application, an ultrasound apparatus is provided, comprising: first down-conversion circuitry comprising: first direct digital synthesis (DDS) circuitry configured to generate first waveforms having time-varying frequency content; and wherein the first down-conversion circuitry is configured to shift a first ultrasound signal in a frequency domain using the first waveforms having time-varying frequency content to produce a first frequency-shifted ultrasound signal. The ultrasound apparatus further comprises second down-conversion circuitry comprising: second direct digital synthesis (DDS) circuitry configured to generate second waveforms having time-varying frequency content; and wherein the second down-conversion circuitry is configured to shift a second ultrasound signal in the frequency domain using the second waveforms having time-varying frequency content to produce a second frequency-shifted ultrasound signal. The ultrasound apparatus further comprises control circuitry configured to control the first DDS circuitry and the second DDS circuitry independently such that the first waveforms and the second waveforms are different.

According to an aspect of the present application, an ultrasound apparatus is provided, comprising: down-conversion circuitry comprising: direct digital synthesis (DDS) circuitry configured to generate waveforms having time-varying frequency content; and wherein the down-conversion circuitry is configured to shift an ultrasound signal in a frequency domain using the waveforms having time-varying frequency content to produce a frequency-shifted ultrasound signal. The ultrasound apparatus further comprises receive beamforming circuitry configured to perform receive beamforming on the frequency-shifted ultrasound signal. The down-conversion circuitry is upstream of the receive beamforming circuitry in at least some embodiments.

According to an aspect of the present application, a method is provided, comprising: receiving an ultrasound signal; generating waveforms having time-varying frequency content; shifting the ultrasound signal in a frequency domain using the waveforms having the frequencies that vary in time to produce a frequency-shifted ultrasound signal; filtering the frequency-shifted ultrasound signal to produce a filtered frequency-shifted ultrasound signal; and subsequent to the shifting and the filtering, performing receive beamforming on the filtered frequency-shifted ultrasound signal.

BRIEF DESCRIPTION OF THE DRAWINGS

Various aspects and embodiments will be described with reference to the following exemplary and non-limiting figures. It should be appreciated that the figures are not necessarily drawn to scale. Items appearing in multiple figures are indicated by the same or a similar reference number in all the figures in which they appear.

DETAILED DESCRIPTION

Figure 1:
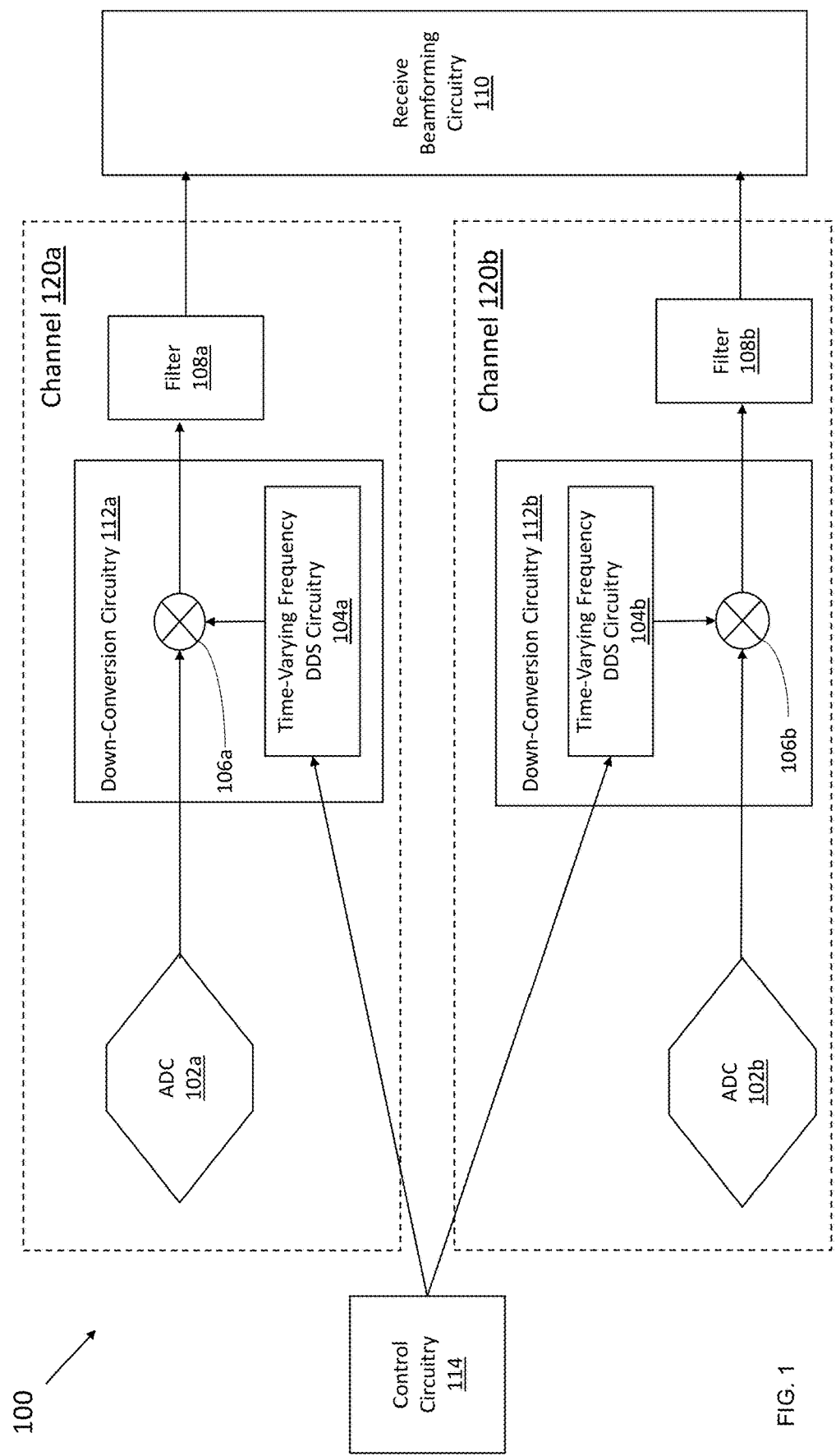
FIG. 1 is a block diagram illustrating example receive circuitry in an ultrasound device, in accordance with certain embodiments described herein.

Recent advances in ultrasound technology have enabled large arrays of ultrasound transducers and ultrasound processing units (UPUs) implemented as integrated circuits to be incorporated onto a semiconductor chip to form an ultrasound-on-chip. Each UPU may include, for example, high-voltage pulsers to drive the ultrasonic transducers to emit ultrasound waves; analog and mixed-signal receiver channels to receive and digitize ultrasound echoes; digital processing circuitry to filter, compress, and/or beamform the digital data from each channel; and digital sequencing circuitry to control and synchronize different parts of the circuitry. An ultrasound-on-chip may include ultrasound transducers and integrated circuits (e.g., UPUs) integrated on a single chip (e.g., a semiconductor chip) or on multiple stacked chips that are packaged together. An ultrasound-on-chip may form the core of a handheld ultrasound probe or an ultrasound device having another form factor such as a wearable ultrasound patch or an ingestible ultrasound pill. For further description of ultrasound-on-chips, see U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application), which is incorporated by reference herein in its entirety.

In some embodiments, the digital processing circuitry of an ultrasound-on-chip may include circuitry for demodulating an ultrasound signal at least in part by: down-converting the ultrasound signal (e.g., modifying the ultrasound signal such that the center frequency of its spectrum is lowered) and then filtering the down-converted ultrasound signal with a filter (e.g., a low-pass filter) to remove undesired frequencies in the ultrasound signal and thereby reduce noise. When the frequency response of the filter matches the frequency spectrum of the signal, such that less of the desired portion (in the frequency domain) of the signal is rejected by the filter and less of the undesired portion (in the frequency domain) of the signal is accepted by the filter, the signal quality (in particular, the signal-to-noise ratio) may be higher. Matching the frequency spectrum of the signal to the frequency response of the filter may include shifting the center frequency of the signal spectrum to align the desired portion of the spectrum relative to the frequency response of the filter. The shifting may be performed by down-conversion circuitry, which may include multiplication by waveforms provided by direct digital synthesis (DDS) circuitry.

However, while the frequency response of the filter may be fixed, the desired and undesired portions of the signal in the frequency domain may vary with time. As an ultrasound wave travels into a body, it may be attenuated exponentially. This attenuation may be frequency dependent such that higher frequencies may be attenuated faster. Accordingly, for signals reflected from progressively deeper depths within the body, the signal spectra may change as the higher frequencies become weaker in proportion to the lower frequencies. In effect, signals that are reflected from progressively deeper depths may have signal spectra in which the desired portions of the signal are shifted progressively to lower frequencies. This may mean that for signals that are reflected from progressively deeper depths, namely signals arriving progressively later, it may be helpful to shift the signal spectrum progressively less in the frequency domain to align the desired portion of the spectrum relative to the frequency response of the filter. By shifting the frequency spectrum of the signal in time to match the frequency response of the filter, the quality of the resulting signal may be improved. To accomplish this, the inventors have recognized that down-converting the signal by multiplying it with waveforms having frequencies that vary linearly with time may enable signals that are arriving progressively later to be shifted progressively less in the frequency domain. Accordingly, the inventors have developed DDS circuitry capable of generating waveforms having time-varying frequencies. Control circuitry may be configured to control parameters of the DDS circuitry, such as the initial frequency of outputted waveforms, final frequency of outputted waveforms, start time for varying the frequency of outputted waveforms, and how fast the frequency of outputted waveforms changes with time. In some embodiments, down-conversion using waveforms having time-varying frequency may be performed on a per-channel basis. In other words, the waveforms having time-varying frequency may be different from channel to channel, such that the frequency shifting as a function of time is different from channel to channel.

The techniques developed by the inventors and described herein may involve demodulating ultrasound signals received by an ultrasound device by using waveforms having time-varying frequency generated by DDS circuitry. In some embodiments, these waveforms having time-varying frequency are not generated for transmission by the ultrasound device; rather they are generated to facilitate processing of ultrasound signals received by the ultrasound device (i.e., ultrasound signals generated by ultrasound transducers in the ultrasound device based on received ultrasound waves). Hence, down-conversion performed using the waveforms with the time-varying frequency may occur prior to receive beamforming.

It should be appreciated that the embodiments described herein may be implemented in any of numerous ways. Examples of specific implementations are provided below for illustrative purposes only. It should be appreciated that these embodiments and the features/capabilities provided may be used individually, all together, or in any combination of two or more, as aspects of the technology described herein are not limited in this respect.

FIG. 1 is a block diagram illustrating example receive circuitry 100 in an ultrasound device, in accordance with certain embodiments described herein. The receive circuitry 100 includes a channel 120a, a channel 120b, control circuitry 114, and receive beamforming circuitry 110. The channel 120a includes an analog-to-digital converter (ADC) 102a, down-conversion circuitry 112a, and a filter 108a. The down-conversion circuitry 112a includes time-varying frequency direct digital synthesis (DDS) circuitry 104a and a multiplier 106a. The channel 120b includes an analog-to-digital converter (ADC) 102b, down-conversion circuitry 112b, and a filter 108b. The down-conversion circuitry 112b includes time-varying frequency direct digital synthesis (DDS) circuitry 104b and a multiplier 106b. In some embodiments, all the circuitry of the receive circuitry 100 may be integrated on a single chip or on one or more chips in a stacked configuration. In some embodiments, some portions of the circuitry of the receive circuitry 100 (e.g., the ADCs 102a and 102b, the down-conversion circuitry 112a and 112b, the filters 108a and 108b, and the control circuitry 114) may be integrated on a single semiconductor chip or on one or more semiconductor chips in a stacked configuration and other portions of the receive circuitry 100 (e.g., the receive beamforming circuitry 110) may be implemented in another electronic device (e.g., a field-programmable gate array (FPGA) device). In any of these embodiments, the one or more semiconductor chips (e.g., which may also be referred to as an ultrasound-on-chip device) may be disposed in an ultrasound device such as a handheld ultrasound probe, or another type of ultrasound device such as a wearable ultrasound patch or an ingestible ultrasound pill. Additionally, in any of these embodiments including another electronic device such as an FPGA device, the electronic device may also be disposed in the ultrasound device.

The ADC 102a is upstream of the down-conversion circuitry 112a. In some embodiments, the output of the ADC 102a may be directly coupled to the input of the multiplier 106a of the down-conversion circuitry 112a, while in other embodiments, there may be other circuitry disposed between the output of the ADC 102a and the input of the multiplier 106a. The output of the time-varying frequency DDS circuitry 104a is coupled to a second input of the multiplier 106a. In some embodiments, the output of the time-varying frequency DDS circuitry 104a may be directly coupled to the second input of the multiplier 106a, while in other embodiments, there may be other circuitry disposed between the output of the time-varying frequency DDS circuitry 104a and the second input of the multiplier 106a. The output of the multiplier 106a is coupled to the input of the filter 108a. In some embodiments, the output of the multiplier 106a may be directly coupled to the input of the filter 108a, while in other embodiments, there may be other circuitry disposed between the output of the multiplier 106a and the input of the filter 108a. The down-conversion circuitry 112a and the filter 108a are upstream of the receive beamforming circuitry 110. In some embodiments, the output of the filter 108a is directly coupled to the input of the receive beamforming circuitry 110, while in others embodiments, there may be other circuitry disposed between the output of the filter 108a and the input of the receive beamforming circuitry 110.

The ADC 102b is upstream of the down-conversion circuitry 112b. In some embodiments, the output of the ADC 102b may be directly coupled to the input of the multiplier 106b of the down-conversion circuitry 112b, while in other embodiments, there may be other circuitry disposed between the output of the ADC 102b and the input of the multiplier 106b. The output of the time-varying frequency DDS circuitry 104b is coupled to a second input of the multiplier 106b. In some embodiments, the output of the time-varying frequency DDS circuitry 104b may be directly coupled to the second input of the multiplier 106b, while in other embodiments, there may be other circuitry disposed between the output of the time-varying frequency DDS circuitry 104b and the second input of the multiplier 106b. The output of the multiplier 106b is coupled to the input of the filter 108b. In some embodiments, the output of the multiplier 106b may be directly coupled to the input of the filter 108b, while in other embodiments, there may be other circuitry disposed between the output of the multiplier 106b and the input of the filter 108b. The down-conversion circuitry 112b and the filter 108b are upstream of the receive beamforming circuitry 110. In some embodiments, the output of the filter 108b is directly coupled to the input of the receive beamforming circuitry 110, while in others embodiments, there may be other circuitry disposed between the output of the filter 108b and the input of the receive beamforming circuitry 110. The control circuitry 114 is coupled to the time-varying frequency DDS circuitry 104a and the time-varying frequency DDS circuitry 104b.

The ADC 102a, the down-conversion circuitry 112a, and the filter 108a are part of the channel 120a. The ADC 102b, the down-conversion circuitry 112b, and the filter 108b are part of the channel 120b. A channel may include a particular group of ultrasound transducers (not illustrated) and circuitry for processing ultrasound signals received by that particular group of ultrasound transducers. In some embodiments, the ultrasound device may include a two-dimensional array of ultrasound transducers, and each channel may include a particular group of ultrasound transducers in the array. For example, each channel may include a particular group of ultrasound transducers in a column of the array, or in a row of the array. While FIG. 1 illustrates circuitry for two channels, in some embodiments, the receive circuitry 100 may include circuitry for more than two channels (e.g., between 1-10 channels, 10-50 channels, 50-100 channels, 100-500 channels, 500-1000 channels, 1000-2000 channels, or any suitable number of channels). A channel may include more circuitry than illustrated in FIG. 1. Ultrasound transducers in a particular channel may be configured to generate ultrasound signals based on receiving ultrasound waves, and the receive circuitry 100 may be configured to process these ultrasound signals generated by the ultrasound transducers. There may be other circuitry not illustrated in the receive circuitry 100. For example, there may be analog processing circuitry coupled between the ultrasound transducers and the ADCs 102a and 102b. The analog processing circuitry may include, for example, analog amplification circuitry (e.g., transimpedance amplifiers for converting currents from ultrasound transducers to voltages), analog filtering circuitry, analog beamforming circuitry, analog dechirp circuitry, analog quadrature demodulation (AQDM) circuitry, analog time delay circuitry, analog phase shifting circuitry, analog summing circuitry, analog time gain compensation circuitry, and/or analog averaging circuitry. In some embodiments, ultrasound transducers may be directly coupled to the ADCs 102a and 102b.

The ADCs 102a and 102b may be configured to convert analog ultrasound signals (i.e., ultrasound signals generated by ultrasound transducers based on receiving ultrasound waves) to digital ultrasound signals. The ADC 102a may be configured to convert analog ultrasound signals from the channel 120a and the ADC 102b may be configured to covert analog ultrasound signals from the channel 120b. While FIG. 1 illustrates one ADC 102 per channel 120, in some embodiments, the receive circuitry 100 may include more than one ADC 102 per channel 120 (e.g., 2, 3, 4, 5, 6, 7, 8, or any suitable number). Each of the ADCs 102 in a channel 120 may be configured to convert ultrasound signals from one or more particular ultrasound transducers in the channel.

The down-conversion circuitry 112a and 112b may be configured to shift the ultrasound signal from the ADCs 102a and 102b, respectively, in the frequency domain after it has been digitized. For example, if the ultrasound signal from the ADC 102a (or the ADC 102b) occupies a certain band of frequencies, the down-conversion circuitry 112a (or the down-conversion circuitry 112b) may be configured to modify the ultrasound signal from the ADC 102a (or the ADC 102b) in the frequency domain such that the spectrum of the signal shifts to occupy a different band of frequencies, for example a band of frequencies with a lower center frequency.

The time-varying frequency DDS circuitry 104a and 104b may be configured to generate waveforms having time-varying frequency content. For example, the waveforms may have frequencies that vary (e.g., linearly) with time. In some embodiments, the center frequency of such a waveform may decrease with time (when the waveform is a pure sinusoid, then its center frequency is its frequency). In some embodiments, the frequency of such a waveform may increase with time. The control circuitry 114 may be configured to control parameters of the time-varying frequency DDS circuitry 104a and 104b, such as the initial frequency of outputted waveforms, final frequency of outputted waveforms, start time for varying the frequency of outputted waveforms, and how fast the frequency of outputted waveforms changes with time. The control circuitry 114 may be configured to control the time-varying frequency DDS circuitry 104a to use different parameters than the time-varying frequency DDS circuitry 104b, such that the waveforms generated by the time-varying frequency DDS circuitry 104a are different than the waveforms generated by the time-varying frequency DDS circuitry 104b. Thus, the control circuitry 114 may be configured to control the time-varying frequency DDS circuitry 104a and 104b in different channels (e.g., the channels 120a and 120b) independently such that the time-varying frequency DDS circuitry 104a and 104b generate waveforms that are different from one another.

The down-conversion circuitry 112a and 112b may be configured to shift the ultrasound signal in the frequency domain using quadrature modulation. In particular, the multiplier 106a may be configured to multiply the ultrasound signal from the ADC 102a (after it has been digitized) with the complex signal $e^{-i\omega t}$ using the sinusoidal waveforms generated by the time-varying frequency DDS circuitry 104a. The multiplier 106b may be configured to multiply the ultrasound signal from the ADC 102b (after it has been digitized) with the complex signal $e^{-i\omega t}$ using the sinusoidal waveforms generated by the time-varying frequency DDS circuitry 104b. The parameter ω may be the shift in the center frequency of the ultrasound signal, and may vary in time. Realizing this multiplication may include separately multiplying real and imaginary components of the ultrasound signal by the waveforms having frequency content that varies in time. This multiplication may result in modifying the ultrasound signal from the ADCs 102a and 102b such that the spectrum of the signal shifts to occupy a different band of frequencies, for example a band of frequencies with a lower center frequency. As described above, the waveforms generated by the time-varying frequency DDS circuitry 104a may be different than the time-varying frequency DDS circuitry 104b, and thus the multipliers 106a and the multipliers 106b may perform multiplication using different waveforms such that the ultrasound signals from the ADC 102a shift differently than the ultrasound signals from the ADC 102b. For example, the parameter ω of the waveforms used for multiplication by the multipliers 106a and 106b for shifting the ultrasound signals from the ADC 102a and the ADC 102b, respectively, may vary differently as a function of time. Thus, the down-conversion circuitry 112a and 112b may be configured to shift ultrasound signals in different channels (e.g., the channels 120a and 120b) differently, such that the shift in frequency over time is different from one channel to another.

The filters 108a and 108b may be configured to filter the ultrasound signals in the channels 120a and 120b, respectively, after they has been down-converted. In some embodiments, the filters 108a and 108b may be configured as a low-pass filter to remove undesired frequencies in the ultrasound signal, including high frequency images of the ultrasound signal, in order to reduce noise. In some embodiments, the filters 108a and 108b may be a cascaded integrator-comb (CIC) filter.

When the frequency responses of one of the filters 108a and 108b matches the frequency spectrum of the respective signal, such that that less of the desired portion (in the frequency domain) of the signal is rejected and less of the undesired portion (in the frequency domain) of the signal is accepted, the signal quality (in particular, the signal-to-noise ratio) may be higher. Matching the frequency spectrum of the signal to the frequency response of the filter 108 may include shifting the center frequency of the signal spectrum relative to the frequency response of the filter 108. This may result in the filter 108 accepting the desired portion and rejecting the undesired portion. However, while the frequency response of the filter 108 may be fixed, the desired and undesired portions of the signal in the frequency domain may vary with time. As an ultrasound wave travels into a body, it may become attenuated exponentially. This attenuation may be frequency dependent, such that higher frequencies may be attenuated faster. Accordingly, for signals reflected from progressively deeper depths within the body, the signal spectra may change as the higher frequencies become weaker in proportion to the lower frequencies. In effect, signals that are reflected from progressively deeper depths may have signal spectra in which the desired portions of the signal are shifted progressively to lower frequencies. This may mean that for signal that is reflected from progressively deeper depths, namely signal arriving progressively later, the signal spectrum may need to be shifted progressively less in the frequency domain to align the desired portion of the spectrum relative to the frequency response of the filter 108. To accomplish this, the inventors have recognized that down-converting the signal with a waveform having a frequency that varies linearly with time (generated by the time-varying frequency DDS circuitry 104) may enable signal that is arriving progressively later to be shifted progressively less in the frequency domain. By shifting the frequency spectrum of the signal in time to match the frequency response of the filter 108, the quality of the resulting signal may be improved. As described above, shifting the frequency spectrum of signals in time may be performed on a per-channel basis, such that signals in different channels (e.g., the channels 120a and 120b) may be shifted differently. As one example, parameters for the time-varying frequency waveforms used in shifting the frequency of the signals in the different channels (e.g., the channels 120a and 120b) may have different parameters such as different ramp start and/or end times to align with delays used when combining the different channels (e.g., by the receive beamforming circuitry 110).

The receive beamforming circuitry 110 may be configured to perform receive beamforming on the data received from the channels 120a and 120b. Receive beamforming may include applying delays to the data received from the channels 120a and 120b. The receive beamforming circuitry 110 may be configured to apply different delays to each of the channels 120a and 120b. In some embodiments, the channels 120a and 120b may be multiplexed to the receive beamforming circuitry 110. It should be appreciated that the down-converting circuitry 112a and 112b is upstream of the receive beamforming circuitry 110, such that the frequency shifting performed by the down-converting circuitry 112a and 112b occurs prior to receive beamforming by the receive beamforming circuitry 110.

In some embodiments, the receive beamforming circuitry 110 may be configured to compensate during beamforming for the frequency shifting performed by the down-conversion circuitry (e.g., the down-conversion circuitry 112a and 112b and any other down-conversion circuitry in the ultrasound device). In general, the output waveform from DDS circuitry that has linearly increasing or decreasing frequency may be expressed as the following:

$$s_{DDS}(t) = \begin{cases} \cos\left(2\pi \int^t f_0 + Mx\, dx\right) = \cos\left(2\pi\left(\frac{1}{2}Mt^2 + f_0 t\right) + \phi_0\right) \\ -\sin\left(2\pi \int^t f_0 + Mx\, dx\right) = -\sin\left(2\pi\left(\frac{1}{2}Mt^2 + f_0 t\right) + \phi_0\right) \end{cases},$$

where M is the change in frequency per time (slope), $f_0$ is the initial frequency, and $\phi$ is an arbitrary phase offset. Denote the ultrasound data in a particular channel (e.g., the channels 120a or 120b or any other channels in the ultrasound device) after filtering (e.g., after processing by the filters 108a or 108b or any other filter in the ultrasound device) as $u_k(t)$, where t is time and k is the channel index. To beamform to a specific point of interest based on delay-and-sum, the receive beamforming circuitry 110 may be configured to use delay-and-summing (DAS) to assign beamformed data $u_{DAS}$ to this point as follows:

$$u_{DAS} = \sum_k u_k(t_k) \exp(-j\theta_k) \exp(-j\theta),$$

where $t_k$ is the time instant determined by the wave traveling distance, $\theta_k$ is the phase of the DDS signal for channel k, and $\theta$ is a reference phase which may vary from point to point. The term $\exp(-j\theta_k)$ may compensate for the phase induced during down-conversion by the down-conversion circuitry. Following the notation used above for $s_{DDS}(t)$, $$\theta_k = -2\pi(\tfrac{1}{2}M_k t_k^2 + f_{0,k} t_k) - \phi_{0,k}$$

and accordingly, when using variable-frequency DDS, $$u_{DAS} = \sum_k u_k(t_k) \exp\left[j2\pi\left(\tfrac{1}{2}M_k t_k^2 + f_{0,k} t_k\right) + j\phi_{0,k}\right] \exp(-j\theta).$$

As a comparison, when $M_k=0$, $f_{0,k}=f_0$, and $\phi_{0,k}=\phi_0$, the formula may reduce to $$u_{DAS} = \sum_k u_k(t_k) \exp(j2\pi f_0 t_k) \exp[j(\phi_0 - \theta)],$$

which may apply to beamforming with conventional DDS.

As described above, the receive beamforming circuitry 110 may be configured to compensate for the phase induced during down-conversion by the down-conversion circuitry using multiplication by the term $\exp(-j\theta_k)$. The receive beamforming circuitry 110 may include one or more extra multipliers for performing this multiplication. Because $\theta_k$ may depend on $t_k$, the receive beamforming circuitry 110 may also include circuitry for calculating the distance between a point and a channel and/or interpolation circuitry in case there is not data collected at $t_k$.

While FIG. 1 illustrates one multiplier 106 and one filter 108 per ADC 102, in embodiments in which each channel 120 includes more than one ADC 102, there may be one multiplier 106 and one filter 108 for more than one ADC 102 (e.g., 2, 3, 4, 5, 6, 7, 8, or any suitable number) in each channel 120. For example, there may be one multiplier 106 and one filter 108 for every two ADCs 102 in a channel 120. In this example, each multiplier 106 and filter 108 may be clocked at four times the ADC 102 conversion rate. This may be because the multiplication step may be preceded by transformation of the real valued signal from an ADC 102 into "in phase" (real) and "out of phase" (imaginary) parts. Thus, the output of two ADCs 102 may result in two real and two imaginary signals, for a total of 4 signals that are processed at four times the ADC 102 conversion rate. Each of these signals may then pipeline into the multiplication stage of a single multiplier 106 and then into the filter 108.

In some embodiments, there may be two multipliers 106 for every two ADCs 102 in a channel 120, each multiplier clocked at twice the ADC 102 conversion rate. One multiplier 106 may be configured to multiply the real part of the signals from the two ADCs 102 and one multiplier 106 may be configured to multiply the complex part of the signals from the two ADCs 102. In some embodiments, there may be two multipliers 106 for every ADC 102 in a channel 120, each multiplier clocked at the ADC 102 conversion rate. One multiplier 106 may be configured to multiply the real part of the signal from the ADC 102 and one multiplier 106 may be configured to multiply the complex part of the signal from the ADCs 102.

While FIG. 1 illustrates one instance of time-varying frequency DDS circuitry 104 per channel 120, in some embodiments there may be one instance of time-varying frequency DDS circuitry 104 for more than one channel 120 (e.g., 2, 3, 4, 5, 6, 7, 8, or any suitable number). In such embodiments, one instance of time-varying frequency DDS circuitry 104 may be configured to output unique waveforms to each of the multipliers 106 in the multiple channels 120. For example, there may be one instance of time-varying frequency DDS circuitry 104 for every two channels 120, and if there are two multipliers 106 per channel 120, then each instance of time-varying frequency DDS circuitry 104 may be configured to output four unique waveforms to each of the four multipliers 106 in the two channels 120. In some embodiments, multipliers 106 and/or filters 108 may be shared between channels 120s.

In some embodiments, the receive beamforming circuitry 110 may be part of post-processing circuitry configured to post-process ultrasound data after it has been stored in the memory and may include, for example, circuitry for summing, requantization, noise shaping, waveform removal, image formation, and backend processing. In some embodiments, the receive circuitry 100 may include memory. In some embodiments, the memory may be coupled between the filters 108a and 108b and the receive beamforming circuitry 110 (or, more generally, the post-processing circuitry). The memory may be configured to store ultrasound data after it has been filtered by the filters 108a and 108b. In some embodiments, the memory may be configured as a static random-access memory (SRAM), although other types of memory may be used. In some embodiments, the receive circuitry 100 may include communication circuitry. In some embodiments, the memory may be coupled between the filters 108a and 108b and the communication circuitry and the communication circuitry may be coupled between the memory and the receive beamforming circuitry 110 (or, more generally, the post-processing circuitry). In some embodiments, the memory may be absent, and the communication circuitry may be coupled between the filters 108a and 108b and the receive beamforming circuitry 110 (or, more generally, the post-processing circuitry). The communication circuitry may be configured to transmit data from the memory to the beamforming circuitry 110 (or, more generally, the post-processing circuitry) and may include, for example, circuitry capable of transmitting data over a communications link such as a Universal Serial Bus (USB) communications link, a serializer-deserializer (SerDes) link, or a wireless link (e.g., a link employing the I6 802.11 standard). Thus, the communication circuitry may be coupled to the receive beamforming circuitry 110 through a USB communications link (e.g., a cable) or through a SerDes communications link. In some embodiments, the memory and the communication circuitry may be located on an ultrasound-on-chip while the receive beamforming circuitry 110 and/or other post-processing circuitry may be implemented on a separate electronic device (e.g., a field-programmable gate array (FPGA) device) to which the ultrasound-on-a chip is coupled. The separate electronic device may be disposed within an ultrasound device (e.g., a handheld ultrasound probe, a wearable ultrasound patch, or an ingestible ultrasound pill) or it may be an external electronic device to which the ultrasound device is coupled. In some embodiments, the memory and the communication circuitry may be located within an ultrasound device (e.g., a handheld ultrasound probe, a wearable ultrasound patch, or an ingestible ultrasound pill) but external to the ultrasound-on-chip, while the receive beamforming circuitry 110 and/or other post-processing circuitry may be located on separate electronic device within the ultrasound device or it may located on electronic device external to the ultrasound device to which the ultrasound device is coupled.

In some embodiments, the memory may be coupled between the filters 108a and 108b and the receive beamforming circuitry 110 (or, more generally, the post-processing circuitry) and the receive beamforming circuitry 110 (or, more generally, the post-processing circuitry) may be coupled between the memory and the communication circuitry. In some embodiments, the memory may be absent, and the receive beamforming circuitry 110 (or, more generally, the post-processing circuitry) may be coupled between the filters 108a and 108b and the communication circuitry. In some embodiments, the memory, the receive beamforming circuitry 110 (or more generally, the post-processing circuitry, or portions thereof), and the communication circuitry may be located on an ultrasound-on-chip. In some embodiments, the memory, the receive beamforming circuitry 110 (or more generally, the post-processing circuitry) and the communication circuitry may be located within an ultrasound device (e.g., a handheld ultrasound probe, a wearable ultrasound patch, or an ingestible ultrasound pill) but external to the ultrasound-on-chip.

Figure 2:
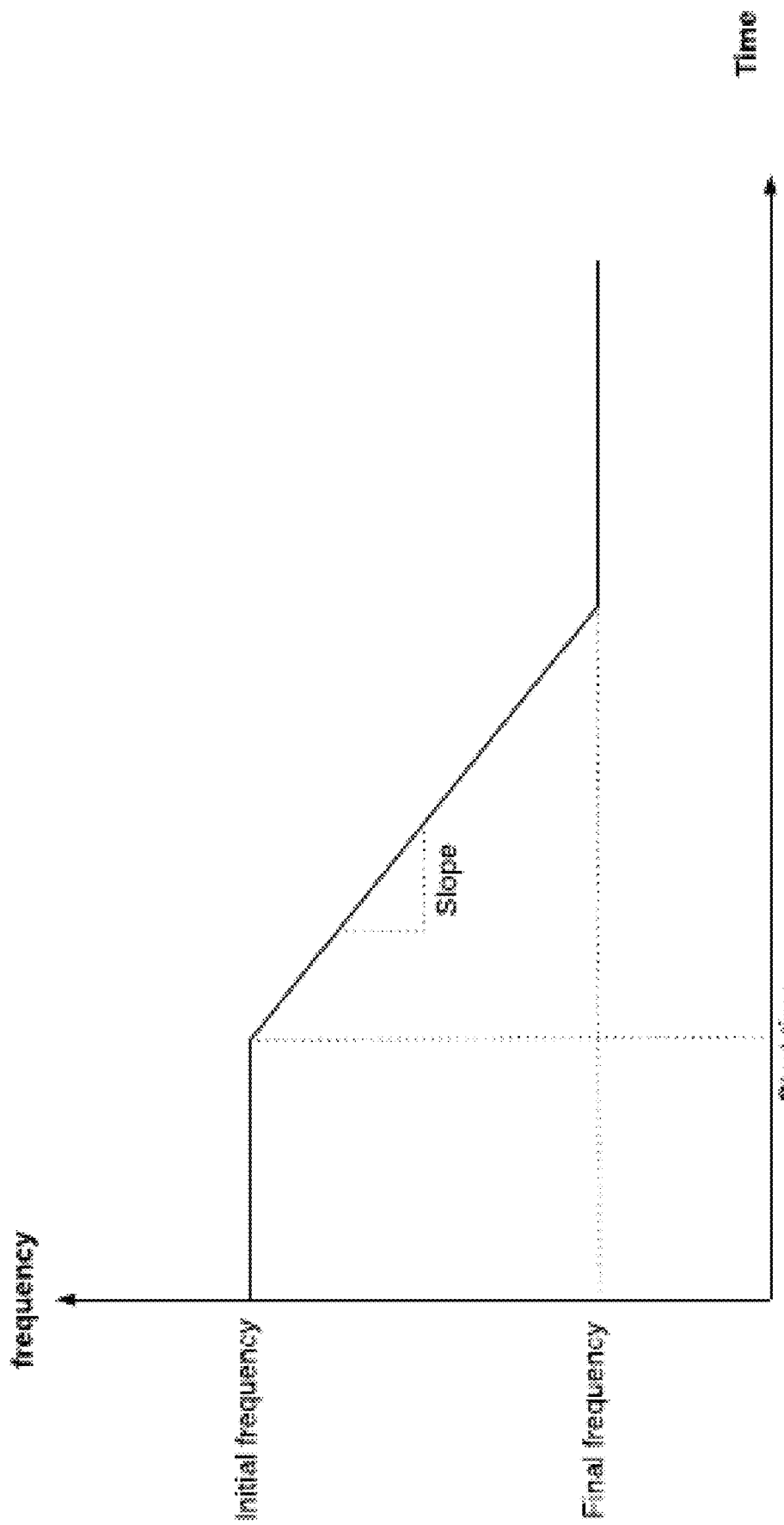
FIG. 2 illustrates an example graph of frequency versus time for a waveform generated by time-varying frequency direct digital synthesis (DDS) circuitry, in accordance with certain embodiments described herein.

Conventional DDS circuitry in an ultrasound device may be configured to generate sinusoidal waveforms having a constant frequency. The inventors have developed DDS circuitry for an ultrasound device that is configured to generate waveforms having frequency that varies with time. FIG. 2 illustrates an example graph of frequency versus time for a waveform generated by time-varying frequency DDS circuitry (e.g., the time-varying frequency DDS circuitry 104), in accordance with certain embodiments described herein. The frequency of the waveform begins at an initial frequency, and at a start time the frequency begins to change to a final frequency. The slope is the rate of change in frequency with time. Once the frequency of the waveform reaches the final frequency, the frequency ceases to change. As described above, control circuitry (e.g., the control circuitry 114) may be configured to control these parameters (initial frequency, final frequency, start time, and slope) of the time-varying frequency DDS circuitry 104a and 104b.

Figure 3:
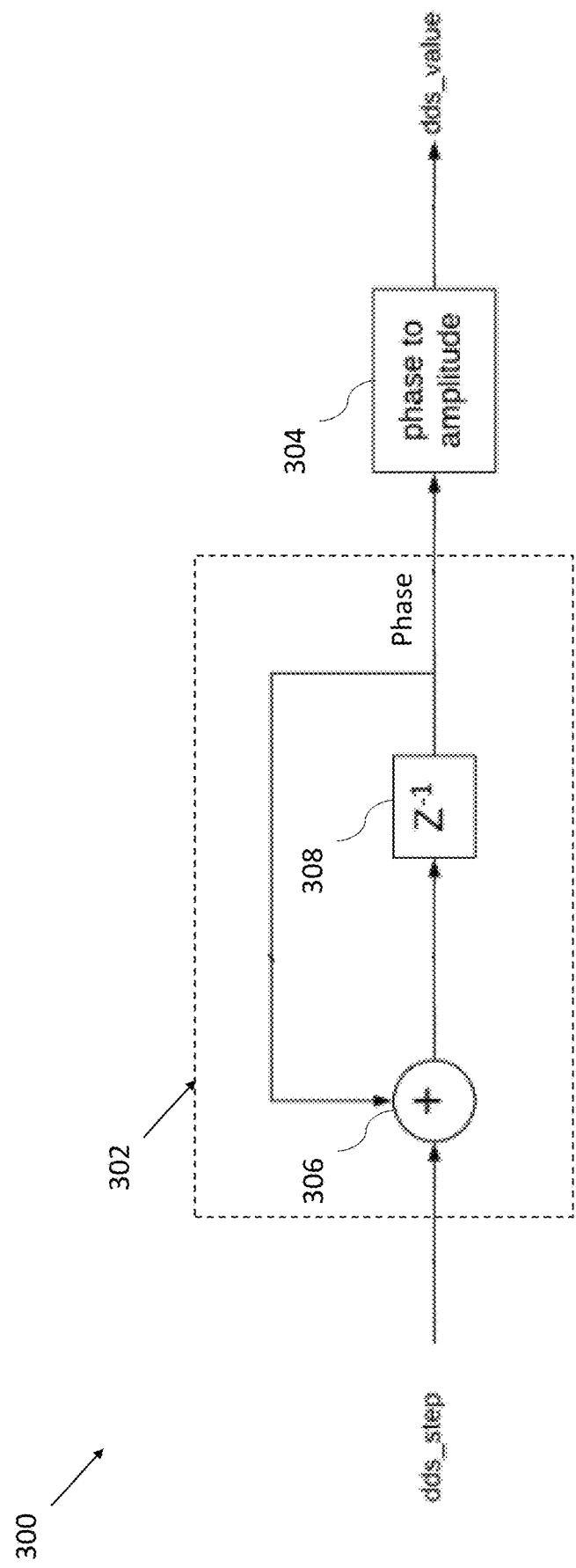
FIG. 3 is a schematic diagram illustrating an example implementation of constant-frequency DDS circuitry.

To illustrate an implementation of time-varying frequency DDS circuitry, it may be helpful to initially describe an implementation of constant-frequency DDS circuitry (i.e., DDS circuitry configured to generate waveforms having a constant frequency with time). FIG. 3 is a schematic diagram illustrating an example implementation of constant-frequency DDS circuitry 300. The constant-frequency DDS circuitry 300 includes a phase accumulator 302 and a phase-to-amplitude converter 304. The phase accumulator 302 includes an adder 306 and a delay block 308. A first input of the adder 306 of the phase accumulator 302 is coupled to an input value (dds_step). A second input of the adder 306 is coupled to the output of the delay block 308 of the phase accumulator 302. The output of the adder 306 is coupled to the input of the delay block 308. The output of the delay block 308 is also coupled to the input of the phase-to-amplitude converter 304. The phase-to-amplitude converter 304 outputs an output value (dds_value), which over time may be a periodic waveform such as a sinusoidal waveform.

In operation, the phase accumulator 302 may generate a new phase value for each cycle (using the delay block 308) that adds (using the adder 306) the previous value of the phase accumulator 302 to dds_step. Thus, the output of the phase accumulator 302 may be a phase signal where each successive phase value is equal to the previous phase value plus dds_step. The phase-to-amplitude converter 304 may be configured to convert the phase values in the phase signal to amplitude values. In other words, the phase-to-amplitude converter 304 may be configured to output the value of a function for which the phase value is the argument. For example, if the current phase value is $\theta$, the phase-to-amplitude converter 304 may output $\sin(\theta)$ or $\cos(\theta)$. In some embodiments, the phase-to-amplitude converter 304 may include a lookup table. In some embodiments, the phase accumulator 302 may be initialized to an arbitrary value such that the initial phase of the output waveform (as outputted by the phase-to-amplitude converter 304) may be set to an arbitrary value.

The phase value (accumulated by the phase accumulator 302) may increase with each cycle, and due to the fixed bit width of the phase value, eventually the phase value may overflow the bit width, return to 0, and increase again. Thus, the phase value may cycle, which may cause the output dds_value to be a periodic waveform. The phase value increases by dds_step each cycle, and the phase value may overflow in fewer cycles with larger dds_step. Thus, a large value for dds_step may result in an output waveform having a larger frequency. When dds_step is constant, the frequency of the output waveform may be constant. The value dds_step (or, generally, the input to the phase accumulator 302) may therefore be considered the frequency input to the DDS circuitry 300 that controls the frequency of the waveform outputted by the DDS circuitry 300.

Figure 4:
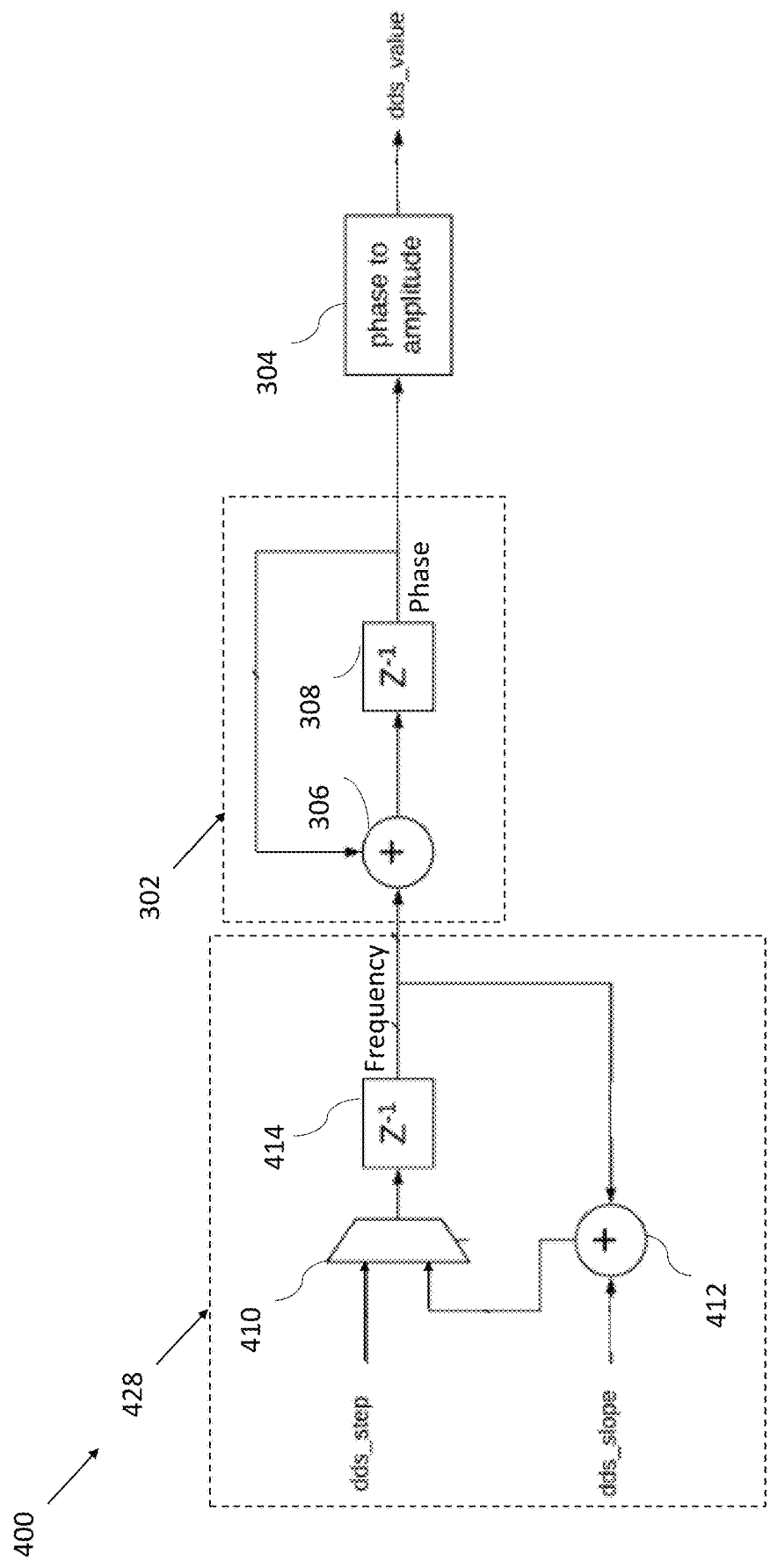
FIG. 4 is a schematic diagram illustrating an example implementation of time-varying frequency DDS circuitry, in accordance with certain embodiments described herein.

FIG. 4 is a schematic diagram illustrating an example implementation of time-varying frequency DDS circuitry 400, in accordance with certain embodiments described herein. The time-varying frequency DDS circuitry 400 may be a partial implementation of circuitry included in the time-varying frequency DDS circuitry 104a and 104b of FIG. 1. The time-varying frequency DDS circuitry 400 is a modification of the constant-frequency DDS circuitry 300 of FIG. 3. The phase accumulator 302 and the phase-to-amplitude converter 304 are in the same configuration as in the constant-frequency DDS circuitry 300. The time-varying frequency DDS circuitry 400 additionally includes a frequency accumulator 428. The frequency accumulator 428 includes a multiplexer 410, an adder 412, and a delay block 414.

A first input of the multiplexer 410 is coupled to dds_step. A second input of the multiplexer 410 is coupled to an output of the adder 412. A first input of the adder 412 is coupled to the value dds_slope. A second input of the adder 412 is coupled to the output of the delay block 414. The output of the multiplexer 410 is coupled to the input of the delay block 414. The output of the delay block 414 is also coupled to the input of the adder 306 of the phase accumulator 302.

In operation, the multiplexer 410 may select whether to output dds_step from its first input or to output a different value, from its second input, that has been modified based on dds_slope. The multiplexer 410 may select the first input when the frequency of the output waveform should not change, and may select the second input when the frequency should change. In particular, the multiplexer 410 may select the second input between the start time (in FIG. 2) and the time when the frequency has reached the final frequency value. Otherwise, the multiplexer 410 may select the first input. Further description of selecting inputs from the multiplexer 410 may be found with reference to FIG. 6.

In the case where the multiplexer 410 selects the first input, the time-varying frequency DDS circuitry 400 operates in a functionally equivalent manner as the constant-frequency DDS circuitry 300. In the case where the multiplexer 410 selects the second input, the frequency accumulator 428 may generate a new frequency value at each cycle (using the delay block 414) that adds (using the adder 412) the previous value of the frequency accumulator 428 to dds_slope. Thus, the output of the frequency accumulator 428 may be a frequency signal where each successive frequency value is equal to the previous frequency value plus dds_slope. The frequency value is the input to the phase accumulator 302, and thus as discussed above, may be considered the frequency input to the time-varying frequency DDS circuitry 400 that controls the frequency of the waveform outputted by the time-varying frequency DDS circuitry 400. Because the frequency value may change with time due to operation of the frequency accumulator 428, the frequency accumulator 428 may cause the time-varying frequency DDS circuitry 400 to output a waveform having a frequency that changes with time. A larger positive value for dds_slope may cause the frequency to increase faster, and a larger negative value for dds_slope may cause the frequency to decrease faster. If the first input to the multiplexer 410 is selected initially, and then the second input is selected, then the frequency value may begin at dds_step (when the first input is selected) and then begin to change (when the second input is selected), then the frequency of the waveform outputted by the time-varying frequency DDS circuitry 400 may initially be constant and the begin to change, as illustrated in FIG. 2.

In general, the output waveform from DDS circuitry that has linearly increasing or decreasing frequency may be expressed as the following:

$$s_{DDS}(t) = \begin{cases} \cos\left(2\pi \int^t f_0 + Mxdx\right) = \cos\left(2\pi\left(\frac{1}{2}Mt^2 + f_0 t\right) + \phi_0\right) \\ -\sin\left(2\pi \int^t f_0 + Mxdx\right) = -\sin\left(2\pi\left(\frac{1}{2}Mt^2 + f_0 t\right) + \phi_0\right) \end{cases},$$

where M is the change in frequency per time (slope), $f_0$ is the initial frequency, and $\phi$ is an arbitrary phase offset.

The initial frequency $f_0$ may be expressed as the following:

$$f_0 = \frac{dds\_step}{2^{DDS\_PHASE\_WIDTH}} f_{ADC},$$

where $f_{ADC}$ is the frequency of the ADCs 102a and 102b and is equivalent to the frequency of each cycle of the DDS circuitry, and DDS_PHASE_WIDTH is the bit width of the phase value in the phase accumulator 302.

The slope M, which is equivalent to the change in frequency per time, can be expressed as the following:

$$M = \frac{dds\_slope}{2^{DDS\_SLOPE\_WIDTH}},$$

where DDS_SLOPE_WIDTH is the bit width of the frequency value in the frequency accumulator 428.

The expression above for the output waveform from DDS circuitry may therefore be expressed as the following:

$$s_{DDS}(t) = \begin{cases} \cos\left[2\pi\left(\frac{1}{2} \cdot \frac{dds\_slope}{2^{DDS\_SLOPE\_WIDTH}} \cdot t^2 + f_{ADC} \cdot \frac{dds\_step}{2^{DDS\_PHASE\_WIDTH}} \cdot t + \phi_0\right)\right] \\ -\sin\left[2\pi\left(\frac{1}{2} \cdot \frac{dds\_slope}{2^{DDS\_SLOPE\_WIDTH}} \cdot t^2 + f_{ADC} \cdot \frac{dds\_step}{2^{DDS\_PHASE\_WIDTH}} \cdot t + \phi_0\right)\right] \end{cases}.$$

The value dds_slope may determine by how much dds_step (and therefore frequency) changes per cycle. Thus, to determine how many integer and fractional bits are needed for dds_slope, it may be necessary to determine the maximum and minimum changes in dds_step per cycle.

The specifications for the DDS circuitry may include the ability to change an output waveform by $\pm f_{min}$ for an imaging depth of $d_{max}$ and the ability to change an output waveform by $\pm f_{max}$ for an imaging depth of $d_{min}$. This first constraint may dictate the minimum change in dds_step per cycle (i.e., the minimum dds_slope) and the second constraint may dictate the maximum change in dds_step per cycle (i.e., the maximum dds_slope). These specifications may be based on a requirement that the center frequency should be able to shift by a certain percentage (e.g., 50%). In particular, the smallest shift may be based on a certain percentage shift in center frequency of the lowest-frequency signal that the ultrasound device may use to image the deepest depth, and the largest shift may be based on a certain percentage shift in center frequency of the highest-frequency signal that the ultrasound device may use to image the shallowest depth. For example, the lowest-frequency signal that the ultrasound device may use to image the deepest depth may be 2 MHz signal to image a depth of 25 cm. The highest-frequency signal that the ultrasound device may use to image the shallowest depth may be 10 MHz to image a depth of 4 cm. Assuming a shift in center frequency of 50%, the specifications based on these example parameters may include the ability to change the output waveform frequency by ±1 MHz for an imaging depth of 25 cm and by ±5 MHz for an imaging depth of 4 cm.

The change in dds_step for a given change in frequency can be expressed as the following:

$$\Delta dds\_step = \frac{\Delta f_0 \cdot 2^{DDS\_PHASE\_WIDTH}}{f_{ADC}}.$$

Regarding the minimum change in dds_step per cycle (i.e., the minimum dds_slope), a change in frequency of $\pm f_{min}$ for an imaging depth of $d_{max}$ may be approximately equivalent to a change in frequency of $\pm f_{min}$ over $t_{max}$ microseconds, where $t_{max}$ microseconds is the time taken by a sound wave to travel back and forth across a depth of $d_{max}$, assuming a value for the speed of sound. For example, for a change in frequency of ±1 MHz, an imaging depth of 25 cm, and assuming the speed of sound is 1500 m/s, $t_{max}$ may be (2·25 cm)/(1500 m/s)≈333 microseconds. The minimum change in dds_step per cycle may occur for the smallest change in frequency over the imaging depth and for the highest ADC frequency. The latter may be true because the smallest change in dds_step per cycle may occur when there are the most cycles during which dds_step over the required time period; the most cycles occur during a time period when the ADC frequency is the highest. Assume a change in frequency of $f_{min}$, a highest ADC frequency of $f_{ADC}$, and a bit width of the phase value in the phase accumulator 302 of DDS_PHASE_WIDTH. Then, the change in dds_step to realize the $f_{min}$ change in frequency is equivalent to $$\frac{f_{min}}{f_{ADC}} \cdot 2^{DDS\_PHASE\_WIDTH}.$$

The change in frequency must occur over $t_{max}$, which is equivalent to $(t_{max} \cdot f_{ADC})$ cycles of the ADC, which runs at $f_{ADC}$. Thus, the minimum change in dds_step per cycle (i.e., the minimum dds_slope) is $$\frac{\frac{f_{min}}{f_{ADC}} \cdot 2^{DDS\_PHASE\_WIDTH}}{t_{max} \cdot f_{ADC}}.$$

If N is the smallest number for which $$\frac{\frac{f_{min}}{f_{ADC}} \cdot 2^{DDS\_PHASE\_WIDTH}}{t_{max} \cdot f_{ADC}} > 2^{-N},$$

then N fractional bits in dds_slope may be sufficient.

Regarding the maximum change in dds_step per cycle (i.e., the maximum dds_slope), a change in frequency of $\pm f_{max}$ for an imaging depth of $d_{min}$ may be approximately equivalent to a change in frequency of $\pm f_{max}$ over $t_{min}$, where $t_{min}$ is the time taken by a sound wave to travel back and forth across a depth of $d_{min}$, assuming a value for the speed of sound. For example, for a change in frequency of ±5 MHz, an imaging depth of 4 cm, and assuming the speed of sound is 1500 m/s, $t_{min}$ may be (2·4 cm)/(1500 m/s)≈53 microseconds. The largest change in frequency of $\pm f_{max}$ implies that the ADC frequency must be at least $2 \cdot f_{max}$ to satisfy the Nyquist criterion (sampling at twice the maximum signal frequency). The maximum change in dds_step per cycle may occur for the slowest ADC frequency. The latter may be true because the largest change in dds_step per cycle may occur when there are the fewest cycles during which dds_step over the required time period; the fewest cycles occur during a time period when the ADC frequency is the lowest. Assume a change in frequency of $f_{max}$, a highest ADC frequency of $2 \times f_{max}$, and a bit width of the phase value in the phase accumulator 302 of DDS_PHASE_WIDTH. Then, the change in dds_step to realize the $f_{max}$ change in frequency is equivalent to $$\frac{f_{max}}{2 \cdot f_{max}} \cdot 2^{DDS\_PHASE\_WIDTH}.$$

The change in frequency must occur over $t_{min}$, which is equivalent to $(t_{min} \cdot 2 \cdot f_{max})$ cycles of the ADC, which runs at $2 \cdot f_{max}$. Thus, the maximum change in dds_step per cycle (i.e., the maximum dds_slope) is $$\frac{\frac{f_{max}}{2 \cdot f_{max}} \cdot 2^{DDS\_PHASE\_WIDTH}}{t_{min} \cdot 2 \cdot f_{max}}. \quad \text{If } \frac{\frac{f_{max}}{2 \cdot f_{max}} \cdot 2^{DDS\_PHASE\_WIDTH}}{t_{min} \cdot 2 \cdot f_{max}} < 1,$$

then no integer bits in dds_slope may be needed. If $$\frac{\frac{f_{max}}{2 \cdot f_{max}} \cdot 2^{DDS\_PHASE\_WIDTH}}{t_{min} \cdot 2 \cdot f_{max}} > 1$$

and L is the smallest number for which $$\frac{\frac{f_{max}}{2 \cdot f_{max}} \cdot 2^{DDS\_PHASE\_WIDTH}}{t_{min} \cdot 2 \cdot f_{max}} < 2^L - 2^{-N},$$

(where N is the number of fractional bits in dds_slope), then L integer bits in dds_slope may be sufficient.

Figure 5:
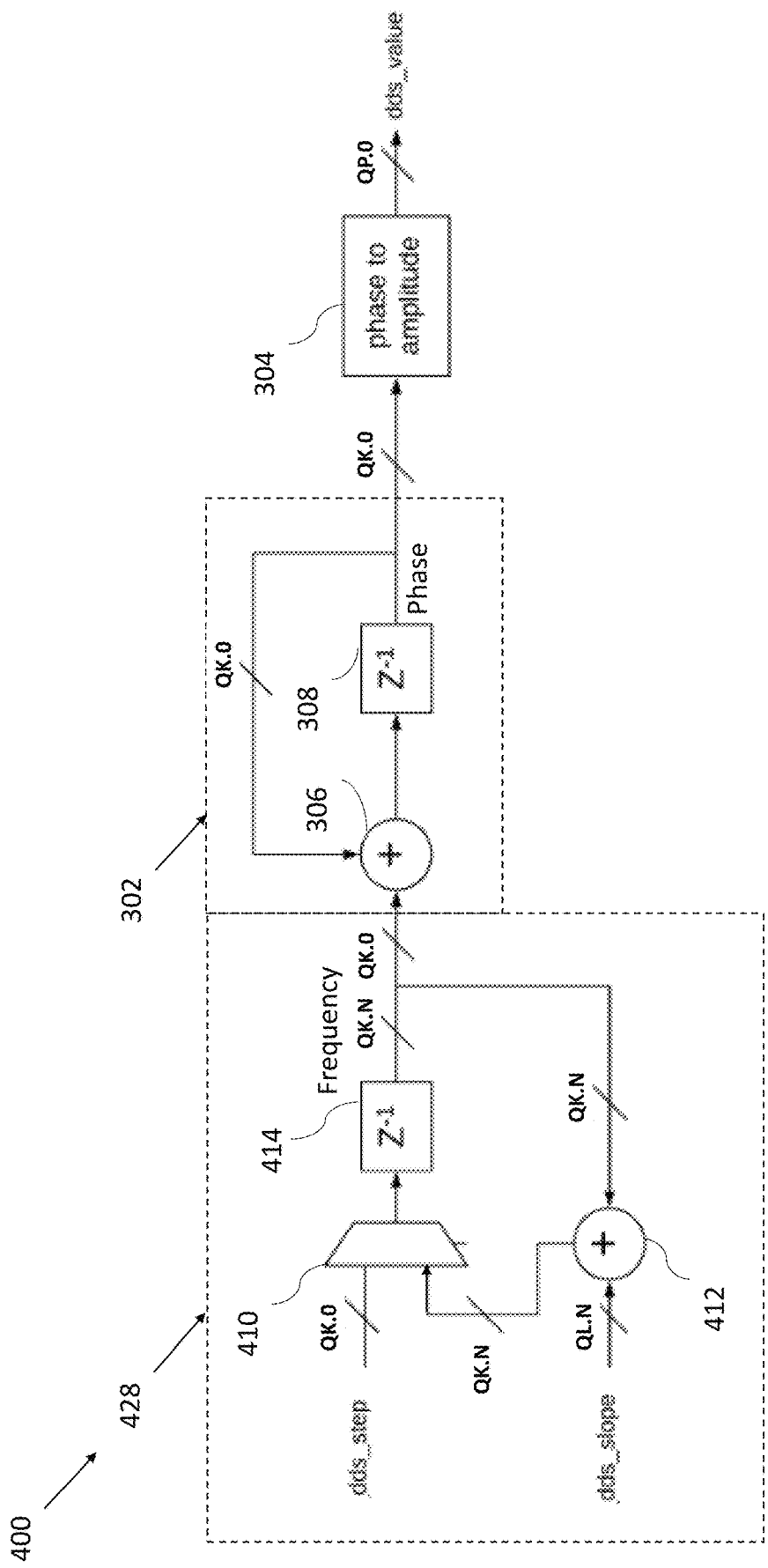
FIG. 5 is a schematic diagram illustrating example bit widths for values in the time-varying frequency DDS circuitry of FIG. 4, in accordance with certain embodiments described herein.

FIG. 5 is a schematic diagram illustrating example bit widths for values in the time-varying frequency DDS circuitry 400, in accordance with certain embodiments described herein. The bit widths are illustrated using standard Q notation, where the number to the left of the period is the number of integer bits and the number to the right of the period is the number of fractional bits. It can be seen that dds_slope has N fractional bits and L integer bits. The value dds_step has K integer bits and no fractional bits. The sum of dds_slope and dds_step (i.e., the frequency value) has K integer bits and N fractional bits, where L<K. The phase value has K integer bits and no fractional bits (i.e., DDS_PHASE_WIDTH=K). The output of the phase-to-amplitude converter 304 has P (which may be different than K) integer bits and no fractional bits. L and N are non-negative integers (L>=0, N>=0), L and N cannot both be zero, and K and P are positive integers (K>0, P>0). It should be noted that the output of the frequency accumulator 428 (i.e., the frequency value) has K integer bits and N fractional bits while the input to the phase accumulator 302 has K bits and 0 fractional bits. Between these two stages, the fractional bits of the frequency value may be discarded. The fractional bits of the frequency value may continue to accumulate in the frequency accumulator 428. Once the fractional bits overflow to cause an increment in the integer bits of the frequency value, then the integer bits of the input to the phase accumulator 302 may change, causing a change in the frequency of the outputted waveform.

Figure 6:
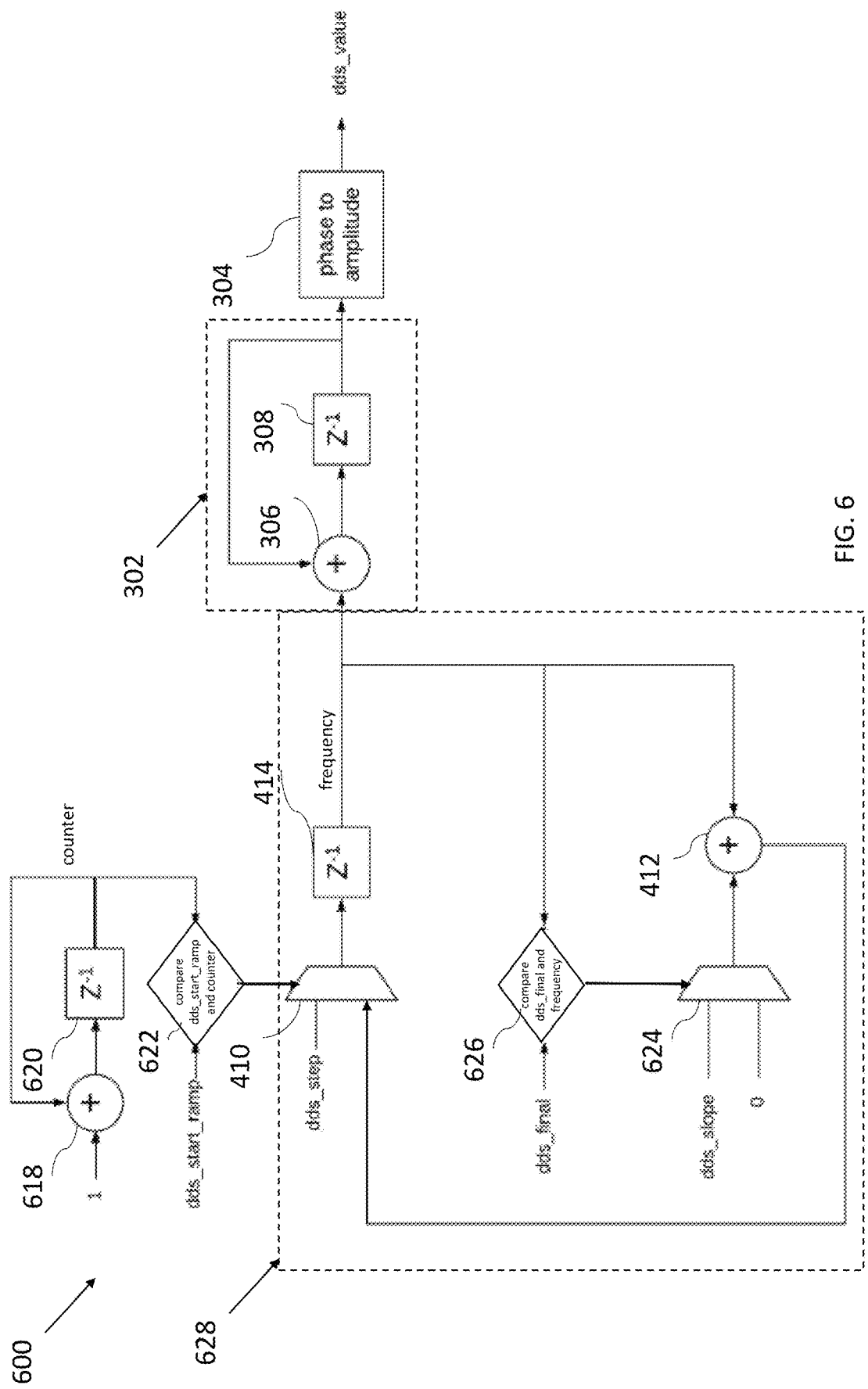
FIG. 6 is a schematic diagram illustrating an example implementation of time-varying frequency DDS circuitry, in accordance with certain embodiments described herein.

FIG. 6 is a schematic diagram illustrating an example implementation of time-varying frequency DDS circuitry 600, in accordance with certain embodiments described herein. The time-varying frequency DDS circuitry 600 may be an implementation of circuitry included in the time-varying frequency DDS circuitry 104a and 104b of FIG. 1. The time-varying frequency DDS circuitry 600 is a fuller implementation of the time-varying frequency DDS circuitry implementation of FIG. 4. The time-varying frequency DDS circuitry 600 includes the phase accumulator 302 and a frequency accumulator 628. The frequency accumulator 628 differs from the frequency accumulator 428 in that the frequency accumulator 628 includes a multiplexer 624 and a decision block 626. The time-varying frequency DDS circuitry 600 further includes an adder 618, a delay block 620, and a decision block 622.

A first input of the multiplexer 624 is coupled to dds_slope. A second input of the multiplexer 624 is coupled to the digital value zero. The output of the multiplexer 624 is coupled to a first input of the adder 412. A first input of the decision block 626 is coupled to a dds_final value. A second input of the decision block 626 is coupled to the output of the delay block 414, namely to the frequency value. The output of the decision block 626 is coupled to the select input of the multiplexer 624. A first input of the adder 618 is coupled to the digital value 1. A second input of the adder 618 is coupled to the output of the delay block 620. The output of the adder 618 is coupled to the input of the delay block 620. The output of the delay block 620 is also coupled to a first input of the decision block 622. A second input of the decision block 622 is coupled to a dds_start_ramp value. The output of the decision block 622 is coupled to the select input of the multiplexer 410.

In operation, the adder 618 and the delay block 620 may operate as a counter. The counter value may increment by 1 every cycle. The decision block 622 may compare the counter value to the dds_final_value. If the counter value is equal to or greater than dds_start_ramp, then the decision block 622 may control the select input of the multiplexer 410 to select the second input of multiplexer 410 (which is coupled to the output of the adder 412). If the counter value is less than dds_start_ramp, then the decision block 622 may control the select input of the multiplexer 410 to select the first input (which is coupled to dds_step). As described above, the multiplexer 410 may select the first input when the frequency of the output waveform should not change, and select the second input when the frequency should change. The value dds_start_ramp may be the number of cycles equivalent to the desired start time when the output waveform frequency should time (i.e., the start time in FIG. 2). The counter value may count how many cycles have elapsed. Thus, when the counter value is equal to or greater than the dds_start_ramp, this may indicate that the start time for changing the output waveform frequency has arrived, and the multiplexer 410 should select the second input so the frequency may change.

The decision block 626 may compare the dds_final value to the frequency value. If dds_slope is negative and the frequency value is equal to or less than dds_final, then the decision block 626 may control the select input of the multiplexer 624 to select the first input (which is coupled to dds_slope). If dds_slope is negative and the frequency value is greater than dds_final, then the decision block 626 may control the select input of the multiplexer 624 to select the second input (which is coupled to 0). The dds_final value may be equal to the frequency value that results in the DDS circuitry producing a waveform having the desired final frequency (i.e., the final frequency in FIG. 2). As described above, the multiplexer 410 may select the second input when the frequency of the output waveform should change. If the frequency value has not yet reached dds_final, then the decision block 626 may control the multiplexer 624 to select the first input. This may cause the sum of dds_slope and the most recent frequency value (i.e., from the output of the adder 412) to be inputted to the second input of the multiplexer 410, and this may cause the change in frequency to occur, as described above. However, when the dds_final value has reached to the frequency value that results in the DDS circuitry producing a waveform having the desired final frequency (i.e., the final frequency in FIG. 2), the frequency of the output waveform should not change. Accordingly, the decision block 626 may control the multiplexer 624 to select the second input. This may cause the sum of 0 and the most recent frequency value (i.e., from the output of the adder 412) to be inputted to the second input of the multiplexer 410. Thus, the value at the second input of the multiplexer 410 may not change further from the most recent frequency value, and this may cause the frequency of the outputted waveform to not change further.

It should be appreciated that control circuitry (e.g., the control circuitry 114) may be configured to control the time-varying frequency DDS circuitry 600, and in particular initial frequency of outputted waveforms, final frequency of outputted waveforms, start time for varying the frequency of outputted waveforms, and how fast the frequency of outputted waveforms changes with time, by supplying parameters such as dds_step, dds_slope, dds_final, and dds_start_ramp. It should also be appreciated that the implementations of DDS circuitry illustrated in FIGS. 3-6 are non-limiting, and other implementations performing the same functions may also be used.

Figure 7:
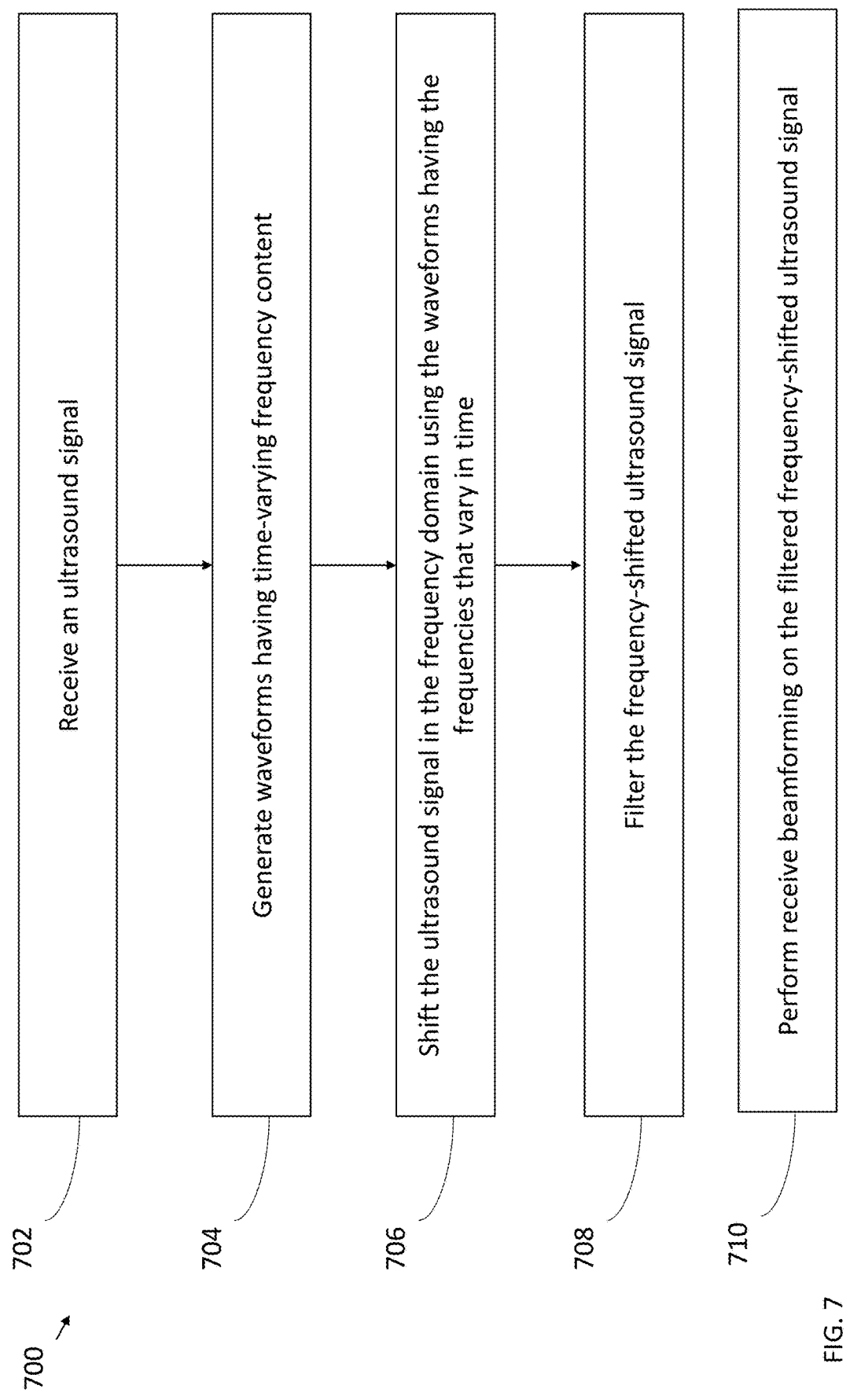
FIG. 7 is a flow diagram illustrating a process for processing ultrasound signals, in accordance with certain embodiments described herein.

FIG. 7 is a flow diagram illustrating a process 700 for processing ultrasound signals, in accordance with certain embodiments described herein. The process 700 may be performed by receive circuitry (e.g., the receive circuitry 100). In some embodiments, the receive circuitry may be disposed on an ultrasound-on-chip in an ultrasound device. In some embodiments, portions of the receive circuitry (e.g., the ADC, down-conversion circuitry, filter, and control circuitry) may be disposed on an ultrasound-on-chip and portions (e.g., receive beamforming circuitry) may be disposed in the ultrasound device external to the ultrasound-on-chip. In some embodiments, portions of the receive circuitry (e.g., the ADC, down-conversion circuitry, filter, and control circuitry) may be disposed on an ultrasound-on-chip and portions (e.g., receive beamforming circuitry) may be disposed in an electronic device external to the ultrasound device.

The process 700 begins with act 702. In act 702, the receive circuitry receives an ultrasound signal. For example, the receive circuitry may receive an analog ultrasound signal from one or more ultrasound transducers. The ultrasound transducers may have generated the analog ultrasound signals based on receiving ultrasound waves. Receiving the ultrasound signal may include converting an analog ultrasound signal to a digital ultrasound signal using an ADC (e.g., the ADCs 102a or 102b) in the receive circuitry. In some embodiments, the receive circuitry may receive different ultrasound signals from different channels. The process 700 proceeds from act 702 to act 704.

In act 704, the receive circuitry generates waveforms having time-varying frequency content. In other words, the waveforms may include frequencies that vary in time. In some embodiments, DDS circuitry (e.g., the time-varying frequency DDS circuitry 104a, 104b, 400, and/or 600) in down-conversion circuitry (e.g., the down-conversion circuitry 112a or 112b) may generate these waveforms. In some embodiments, control circuitry (e.g., the control circuitry 114) may control the DDS circuitry to control parameters of the outputted waveforms, such as the initial frequency, final frequency, start time for varying the frequency, and how fast the frequency changes with time. In some embodiments, the control circuitry may control DDS circuitry in different channels independently such that the outputted waveforms from different channels are different (e.g., have different parameters). The process 700 proceeds from act 704 to act 706.

In act 706, the receive circuitry shifts the ultrasound signal (received in act 702) in the frequency domain using the waveforms having the frequencies that vary in time (generated in act 704). In some embodiments, the down-conversion circuitry may be configured to shift the ultrasound signal in the frequency domain using quadrature modulation. In particular, a multiplier (e.g., the multiplier 106a or 106b) may be configured to multiply an ultrasound signal from an ADC after it has been digitized with the complex signal $e^{-i\omega t}$ using the sinusoidal waveforms generated by the time-varying frequency DDS circuitry in act 704. ω may be a shift in the center frequency of the ultrasound signal, and may vary in time. Realizing this multiplication may include separately multiplying real and imaginary components of the ultrasound signal by the waveforms having frequencies that vary in time. In some embodiments, one multiplier may multiply both the real and complex parts of the signal. In some embodiments, one multiplier may multiple the real part and one multiplier may multiply the complex part. This multiplication may result in modifying the ultrasound signal from the ADCs such that the spectrum of the signal shifts to occupy a different band of frequencies, for example a band of frequencies with a lower center frequency. The receive circuitry may frequency shift signals in different channels differently using different waveforms generated in act 704 for each channel, such that the frequency shifting in time for one channel is different than the frequency shifting in time for another channel. The process 700 proceeds from act 706 to act 708.

In act 708, the receive circuitry filters the frequency-shifted ultrasound signal. In some embodiments, a filter in the receive circuitry (e.g., the filter 108a or 108b), which may be, for example, a CIC filter, may perform the filtering. The filter may perform low-pass filtering to remove undesired frequencies in the ultrasound signal, including high frequency images of the ultrasound signal, in order to reduce noise.

When the frequency response of the filter matches the frequency spectrum of the signal, such that that less of the desired portion (in the frequency domain) of the signal is rejected and less of the undesired portion (in the frequency domain) of the signal is accepted, the signal quality (in particular, the signal-to-noise ratio) may be higher. Matching the frequency spectrum of the signal to the frequency response of the filter may include shifting the center frequency of the signal spectrum relative to the frequency response of the filter. This may result in the filter accepting the desired portion and rejecting the undesired portion. However, while the frequency response of the filter may be fixed, the desired and undesired portions of the signal in the frequency domain may vary with time. As an ultrasound wave travels into a body, it may become attenuated exponentially. This attenuation may be frequency dependent, such that higher frequencies may be attenuated faster. Accordingly, for signals reflected from progressively deeper depths within the body, the signal spectra may change as the higher frequencies become weaker in proportion to the lower frequencies. In effect, signals that are reflected from progressively deeper depths may have signal spectra in which the desired portions of the signal are shifted progressively to lower frequencies. This may mean that for signal that is reflected from progressively deeper depths, namely signal arriving progressively later, the signal spectrum may need to be shifted progressively less in the frequency domain to align the desired portion of the spectrum relative to the frequency response of the filter. Multiplying the ultrasound signal with a waveform having a frequency that varies linearly with time (at act 706) may enable signal that is arriving progressively later to be shifted progressively less in the frequency domain. This may help in aligning the desired portion of the spectrum relative to the frequency response of the filter performing the filtering in act 708. By shifting the frequency spectrum of the signal in time to match the frequency response of the filter, the quality of the resulting signal may be improved. The process 700 proceeds from act 708 to act 710.

In act 710, the receive circuitry performs receive beamforming on the filtered frequency-shifted signal (i.e., the signal produced in act 708). In some embodiments, receive beamforming circuitry (e.g., the receive beamforming circuitry 110) in the receive circuitry 100 may perform the receive beamforming. Receive beamforming may include applying delays to the filtered frequency-shifted signal. In some embodiments, the receive beamforming performed at act 710 may include compensating for the frequency shifting performed in act 706. It should be appreciated that the frequency shifting in act 706 is performed prior to receive beamforming in act 710. In some embodiments, act 704 may occur before act 702. In some embodiments, acts 702 and 704 may occur in parallel.

Figure 8:
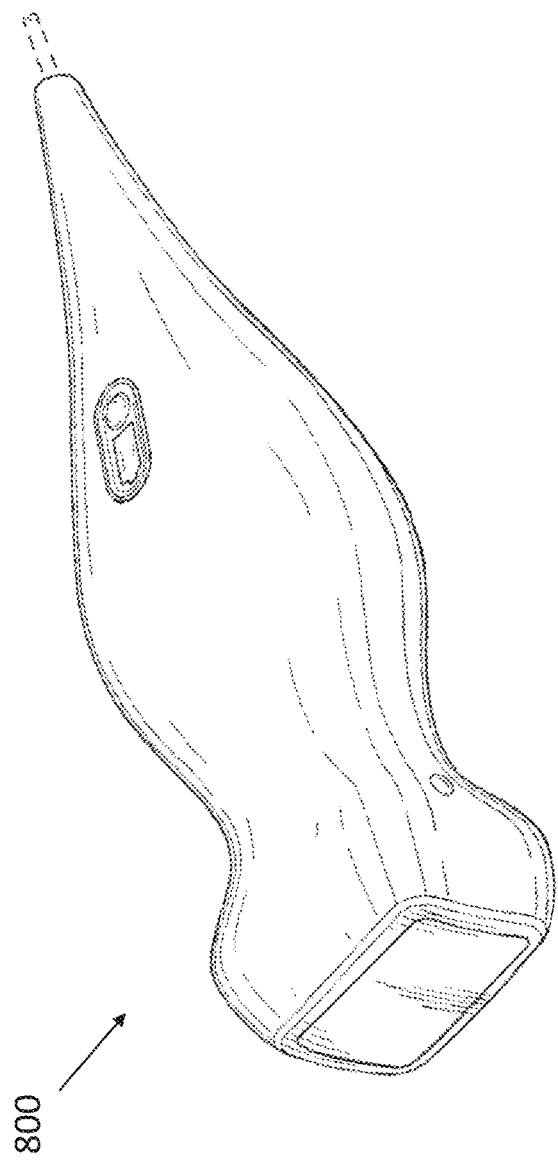
FIG. 8 illustrates an example handheld ultrasound probe, in accordance with certain embodiments described herein.

FIG. 8 illustrates an example handheld ultrasound probe 800, in accordance with certain embodiments described herein. In some embodiments, an ultrasound-on-chip including ADCs (e.g., the ADCs 102a and 102b), down-conversion circuitry (e.g., the down-conversion circuitry 112a and 112b), filters (e.g., the filters 108a and 108b), and receive beamforming circuitry (e.g., the receive beamforming circuitry 110) may be disposed in the handheld ultrasound probe 800. In some embodiments, an ultrasound-on-chip including ADCs (e.g., the ADCs 102a and 102b), down-conversion circuitry (e.g., the down-conversion circuitry 112a and 112b), and filters (e.g., the filters 108a and 108b), and another electronic device (e.g., an FPGA) including receive beamforming circuitry (e.g., the receive beamforming circuitry 110) may be disposed in the handheld ultrasound probe 800. In some embodiments, an ultrasound-on-chip including ADCs (e.g., the ADCs 102a and 102b), down-conversion circuitry (e.g., the down-conversion circuitry 112a and 112b), and filters (e.g., the filters 108a and 108b), may be disposed in the handheld ultrasound probe 800, and the handheld ultrasound probe 800 may be coupled (e.g., through a wired and/or wireless connection) to an external electronic device including receive beamforming circuitry (e.g., the receive beamforming circuitry 110).

Figure 9:
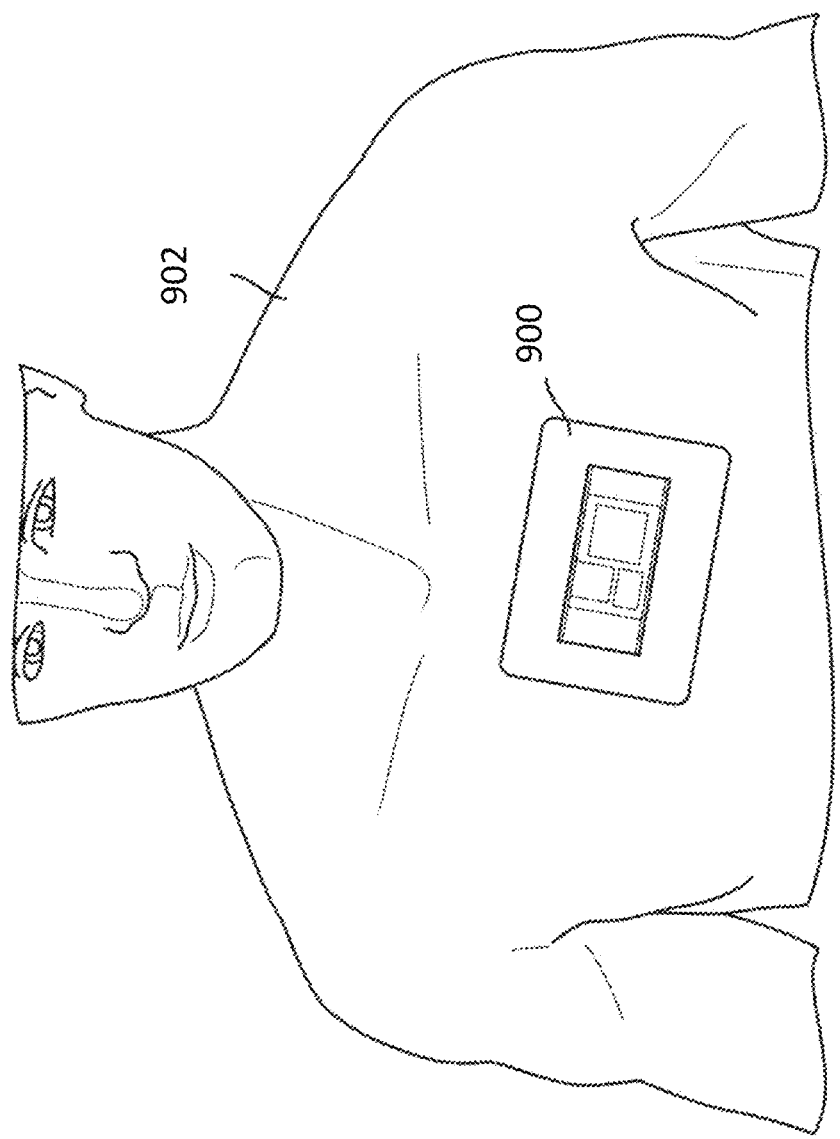
FIG. 9 illustrates an example wearable ultrasound patch, in accordance with certain embodiments described herein.

FIG. 9 illustrates an example wearable ultrasound patch 900, in accordance with certain embodiments described herein. The wearable ultrasound patch 900 is coupled to a subject 902. In some embodiments, an ultrasound-on-chip including ADCs (e.g., the ADCs 102a and 102b), down-conversion circuitry (e.g., the down-conversion circuitry 112a and 112b), filters (e.g., the filters 108a and 108b), and receive beamforming circuitry (e.g., the receive beamforming circuitry 110) may be disposed in the wearable ultrasound patch 900. In some embodiments, an ultrasound-on-chip including ADCs (e.g., the ADCs 102a and 102b), down-conversion circuitry (e.g., the down-conversion circuitry 112a and 112b), and filters (e.g., the filters 108a and 108b), and another electronic device (e.g., an FPGA) including receive beamforming circuitry (e.g., the receive beamforming circuitry 110) may be disposed in the wearable ultrasound patch 900. In some embodiments, an ultrasound-on-chip including ADCs (e.g., the ADCs 102a and 102b), down-conversion circuitry (e.g., the down-conversion circuitry 112a and 112b), and filters (e.g., the filters 108a and 108b), may be disposed in the wearable ultrasound patch 900, and the wearable ultrasound patch 900 may be coupled (e.g., through a wireless connection) to an external electronic device including receive beamforming circuitry (e.g., the receive beamforming circuitry 110).

Figure 10:
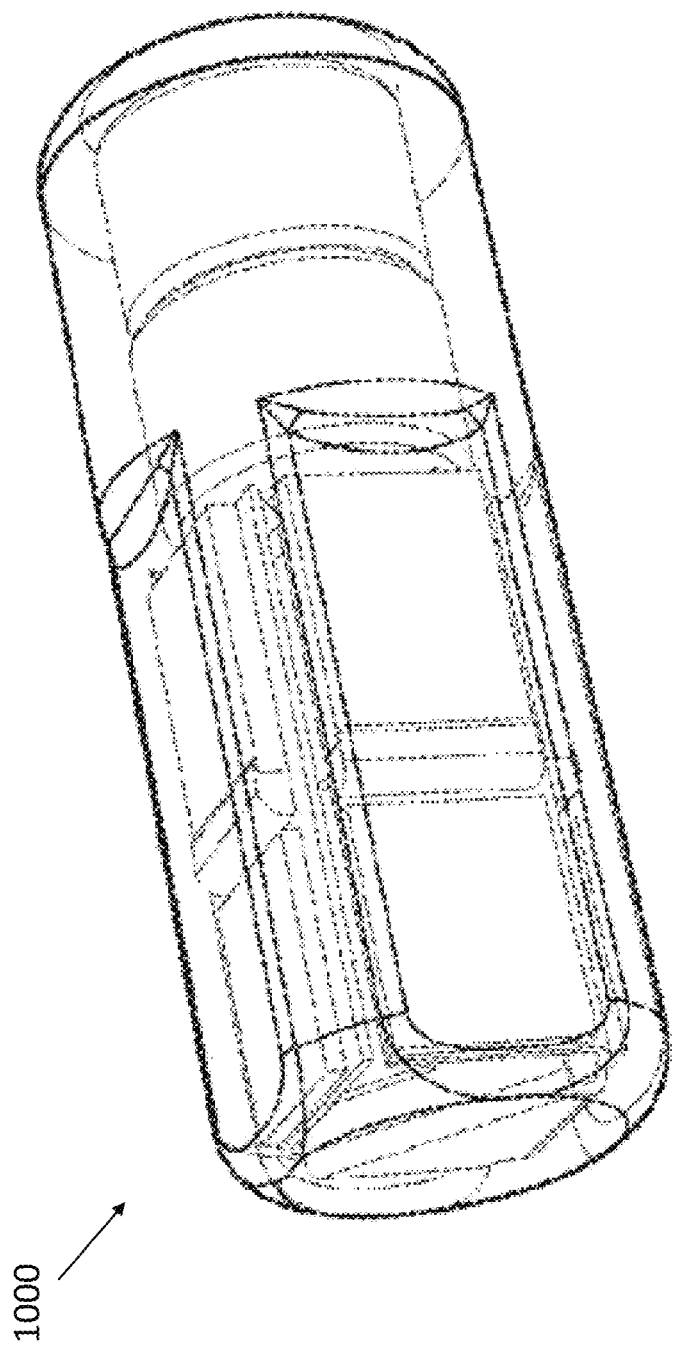
FIG. 10 illustrates an example ingestible ultrasound pill, in accordance with certain embodiments described herein.

FIG. 10 illustrates an example ingestible ultrasound pill 1000, in accordance with certain embodiments described herein. In some embodiments, an ultrasound-on-chip including ADCs (e.g., the ADCs 102a and 102b), down-conversion circuitry (e.g., the down-conversion circuitry 112a and 112b), filters (e.g., the filters 108a and 108b), and receive beamforming circuitry (e.g., the receive beamforming circuitry 110) may be disposed in the ingestible ultrasound pill 1000. In some embodiments, an ultrasound-on-chip including ADCs (e.g., the ADCs 102a and 102b), down-conversion circuitry (e.g., the down-conversion circuitry 112a and 112b), and filters (e.g., the filters 108a and 108b), and another electronic device (e.g., an FPGA) including receive beamforming circuitry (e.g., the receive beamforming circuitry 110) may be disposed in the ingestible ultrasound pill 1000. In some embodiments, an ultrasound-on-chip including ADCs (e.g., the ADCs 102a and 102b), down-conversion circuitry (e.g., the down-conversion circuitry 112a and 112b), and filters (e.g., the filters 108a and 108b), may be disposed in the ingestible ultrasound pill 1000, and the ingestible ultrasound pill 1000 may be coupled (e.g., through a wireless connection) to an external electronic device including receive beamforming circuitry (e.g., the receive beamforming circuitry 110).

Further description of the handheld ultrasound probe 800, the wearable ultrasound patch 900, and the ingestible ultrasound pill 1000 may be found in U.S. patent application Ser. No. 15/626,711 titled "UNIVERSAL ULTRASOUND IMAGING DEVICE AND RELATED APPARATUS AND METHODS," filed on Jun. 19, 2017 and published as U.S. Pat. App. Publication No. 2017-0360399 A1 (and assigned to the assignee of the instant application).

Various inventive concepts may be embodied as one or more processes, of which examples have been provided. The acts performed as part of each process may be ordered in any suitable way. Thus, embodiments may be constructed in which acts are performed in an order different than illustrated, which may include performing some acts simultaneously, even though shown as sequential acts in illustrative embodiments. Further, one or more of the processes may be combined and/or omitted, and one or more of the processes may include additional steps.

Various aspects of the present disclosure may be used alone, in combination, or in a variety of arrangements not specifically described in the embodiments described in the foregoing and is therefore not limited in its application to the details and arrangement of components set forth in the foregoing description or illustrated in the drawings. For example, aspects described in one embodiment may be combined in any manner with aspects described in other embodiments.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

As used herein, reference to a numerical value being between two endpoints should be understood to encompass the situation in which the numerical value can assume either of the endpoints. For example, stating that a characteristic has a value between A and B, or between approximately A and B, should be understood to mean that the indicated range is inclusive of the endpoints A and B unless otherwise noted.

The terms "approximately" and "about" may be used to mean within ±20% of a target value in some embodiments, within ±10% of a target value in some embodiments, within ±5% of a target value in some embodiments, and yet within ±2% of a target value in some embodiments. The terms "approximately" and "about" may include the target value.

Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

Having described above several aspects of at least one embodiment, it is to be appreciated various alterations, modifications, and improvements will readily occur to those skilled in the art. Such alterations, modifications, and improvements are intended to be object of this disclosure. Accordingly, the foregoing description and drawings are by way of example only.

What is claimed is:

1. An ultrasound apparatus, comprising:
   first down-conversion circuitry comprising:
      first direct digital synthesis (DDS) circuitry configured to generate first waveforms having first time-varying frequency content; and
      wherein the first down-conversion circuitry is configured to shift a first ultrasound signal in a frequency domain using the first waveforms having the first time-varying frequency content to produce a first frequency-shifted ultrasound signal;
   second down-conversion circuitry comprising:
      second direct digital synthesis (DDS) circuitry configured to generate second waveforms having second time-varying frequency content; and
      wherein the second down-conversion circuitry is configured to shift a second ultrasound signal in the frequency domain using the second waveforms having the second time-varying frequency content to produce a second frequency-shifted ultrasound signal;

control circuitry configured to control the first DDS circuitry and the second DDS circuitry independently such that the first waveforms and the second waveforms are different;

one or more first ultrasound transducers configured to generate the first ultrasound signal based on receiving first ultrasound waves;

one or more second ultrasound transducers configured to generate the second ultrasound signal based on receiving second ultrasound waves; and wherein the one or more first ultrasound transducers and the one or more second ultrasound transducers are in a two-dimensional array of ultrasound transducers.

2. The ultrasound apparatus of claim 1, wherein the one or more first ultrasound transducers, the one or more second ultrasound transducers, the first down-conversion circuitry, the second down-conversion circuitry, and the control circuitry are integrated on a single semiconductor chip or one or more semiconductor chips in a stacked configuration.

3. The ultrasound apparatus of claim 2, wherein the single semiconductor chip or the one or more semiconductor chips in the stacked configuration is disposed in a handheld ultrasound probe.

4. The ultrasound apparatus of claim 1, wherein the control circuitry is configured to control the first DDS circuitry and the second DDS circuitry such that one or more parameters of the first waveforms and the second waveforms including initial frequency, final frequency, start time for frequency variation, and/or how fast frequency changes with time, are different.

5. The ultrasound apparatus of claim 1, wherein the first down-conversion circuitry is configured to use quadrature modulation to shift the first ultrasound signal in the frequency domain using the first waveforms having the first time-varying frequency content.

6. The ultrasound apparatus of claim 1, further comprising:
a first low-pass filter configured to filter the first frequency-shifted ultrasound signal; and
a second low-pass filter configured to filter the second frequency-shifted ultrasound signal.

7. The ultrasound apparatus of claim 1, wherein the first down-conversion circuitry further comprises a multiplier configured to multiply real and imaginary portions of the first ultrasound signal by the first waveforms having the first time-varying frequency content.

8. The ultrasound apparatus of claim 1, wherein the first down-conversion circuitry and the second down-conversion circuitry are configured to shift the first ultrasound signal and the second ultrasound signals, respectively, in the frequency domain differently, such that a first shift of the first ultrasound signal in frequency over time is different than a second shift of the second ultrasound signal in frequency over time.

9. An ultrasound apparatus, comprising:
first down-conversion circuitry comprising:
first direct digital synthesis (DDS) circuitry configured to generate first waveforms having first time-varying frequency content; and
wherein the first down-conversion circuitry is configured to shift a first ultrasound signal in a frequency domain using the first waveforms having the first time-varying frequency content to produce a first frequency-shifted ultrasound signal;

second down-conversion circuitry comprising:
second direct digital synthesis (DDS) circuitry configured to generate second waveforms having second time-varying frequency content; and
wherein the second down-conversion circuitry is configured to shift a second ultrasound signal in the frequency domain using the second waveforms having the second time-varying frequency content to produce a second frequency-shifted ultrasound signal; and control circuitry configured to control the first DDS circuitry and the second DDS circuitry independently such that the first waveforms and the second waveforms are different, wherein the first DDS circuitry is configured to generate the first waveforms having the first time-varying frequency content by generating waveforms having center frequencies that vary linearly in time.

10. An ultrasound apparatus, comprising:
first down-conversion circuitry comprising:
first direct digital synthesis (DDS) circuitry configured to generate first waveforms having first time-varying frequency content; and
wherein the first down-conversion circuitry is configured to shift a first ultrasound signal in a frequency domain using the first waveforms having the first time-varying frequency content to produce a first frequency-shifted ultrasound signal;

second down-conversion circuitry comprising:
second direct digital synthesis (DDS) circuitry configured to generate second waveforms having second time-varying frequency content; and
wherein the second down-conversion circuitry is configured to shift a second ultrasound signal in the frequency domain using the second waveforms having the second time-varying frequency content to produce a second frequency-shifted ultrasound signal; and control circuitry configured to control the first DDS circuitry and the second DDS circuitry independently such that the first waveforms and the second waveforms are different, wherein the first DDS circuitry is configured to generate the first waveforms having the first time-varying frequency content by generating waveforms having center frequencies that decrease in time.

11. An ultrasound apparatus, comprising:
first down-conversion circuitry comprising:
first direct digital synthesis (DDS) circuitry configured to generate first waveforms having first time-varying frequency content; and
wherein the first down-conversion circuitry is configured to shift a first ultrasound signal in a frequency domain using the first waveforms having the first time-varying frequency content to produce a first frequency-shifted ultrasound signal;

second down-conversion circuitry comprising:
second direct digital synthesis (DDS) circuitry configured to generate second waveforms having second time-varying frequency content; and
wherein the second down-conversion circuitry is configured to shift a second ultrasound signal in the frequency domain using the second waveforms having the second time-varying frequency content to produce a second frequency-shifted ultrasound signal; and control circuitry configured to control the first DDS circuitry and the second DDS circuitry independently such that the first waveforms and the second waveforms are different, wherein the first DDS circuitry is configured to generate the first waveforms having the first time-varying frequency content by generating waveforms having center frequencies that increase in time.

12. An ultrasound apparatus, comprising:
down-conversion circuitry comprising:
direct digital synthesis (DDS) circuitry configured to generate waveforms having time-varying frequency content; and
wherein the down-conversion circuitry is configured to shift an ultrasound signal in a frequency domain using the waveforms having the time-varying frequency content to
produce a frequency-shifted ultrasound signal;
receive beamforming circuitry configured to perform receive beamforming on the frequency-shifted ultrasound signal;
wherein the down-conversion circuitry is upstream of the receive beamforming circuitry;
one or more ultrasound transducers configured to generate the ultrasound signal based on received ultrasound waves; and
wherein the one or more ultrasound transducers are in a two-dimensional array of ultrasound transducers.

13. The ultrasound apparatus of claim 12, wherein the one or more ultrasound transducers and the down-conversion circuitry are integrated on a single semiconductor chip or one or more semiconductor chips in a stacked configuration.

14. The ultrasound apparatus of claim 13, wherein the receive beamforming circuitry is integrated on the single semiconductor chip or the one or more semiconductor chips in the stacked configuration.

15. The ultrasound apparatus of claim 14, wherein the single semiconductor chip or the one or more semiconductor chips in the stacked configuration is disposed in a handheld ultrasound probe.

16. The ultrasound apparatus of claim 13, wherein the receive beamforming circuitry and the single semiconductor chip or the one or more semiconductor chips in the stacked configuration are disposed in a handheld ultrasound probe.

17. The ultrasound apparatus of claim 16, wherein the receive beamforming circuitry is implemented on a field-programmable gate array (FPGA).

18. An ultrasound apparatus, comprising:
down-conversion circuitry comprising:
direct digital synthesis (DDS) circuitry configured to generate waveforms having time-varying frequency content; and
wherein the down-conversion circuitry is configured to shift an ultrasound signal in a frequency domain using the waveforms having the time-varying frequency content to produce a frequency-shifted ultrasound signal;
receive beamforming circuitry configured to perform receive beamforming on the frequency-shifted ultrasound signal;
wherein the down-conversion circuitry is upstream of the receive beamforming circuitry; and
wherein the receive beamforming circuitry is further configured to compensate for the shift of the ultrasound signal in the frequency domain.

19. A method, comprising:
receiving an ultrasound signal from one or more ultrasound transducers configured to generate the ultrasound signal based on received ultrasound waves, wherein the one or more ultrasound transducers are in a two-dimensional array of ultrasound transducers;
generating, using direct digital synthesis (DDS) circuitry, waveforms having time-varying frequency content;
shifting the ultrasound signal in a frequency domain using the waveforms having the time-varying frequency content to produce a frequency-shifted ultrasound signal; and
subsequent to the shifting, performing receive beamforming on the frequency-shifted ultrasound signal.

\* \* \* \* \*